(12) United States Patent
Noivirt-Brik et al.

(10) Patent No.: US 12,256,686 B2
(45) Date of Patent: *Mar. 25, 2025

(54) COMPOSITIONS, KITS AND METHODS FOR CONTROLLING WEED

(71) Applicant: Weedout Ltd., Nes Ziona (IL)

(72) Inventors: Orly Noivirt-Brik, Givataim (IL); Efrat Lidor-Nili, Nes Ziona (IL)

(73) Assignee: Weedout Ltd., Nes Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/884,362

(22) Filed: May 27, 2020

(65) Prior Publication Data

US 2020/0281139 A1 Sep. 10, 2020

Related U.S. Application Data

(63) Continuation of application No. PCT/IL2018/051301, filed on Nov. 28, 2018.

(60) Provisional application No. 62/591,801, filed on Nov. 29, 2017.

(51) Int. Cl.
*A01H 1/06* (2006.01)

(52) U.S. Cl.
CPC ..................... *A01H 1/06* (2013.01)

(58) Field of Classification Search
None
See application file for complete search history.

(56) References Cited

U.S. PATENT DOCUMENTS

| | | | |
|---|---|---|---|
| 8,437,498 | B2 | 5/2013 | Malsam |
| 11,369,116 | B2 | 6/2022 | Lidor-Nili et al. |
| 11,812,735 | B2 | 11/2023 | Lidor-Nili et al. |
| 2006/0053686 | A1 | 3/2006 | Halwas |
| 2017/0359943 | A1 | 12/2017 | Calleija et al. |
| 2018/0065749 | A1 | 3/2018 | Cantrell |
| 2019/0208790 | A1 | 7/2019 | Lidor-Nili et al. |
| 2020/0275617 | A1 | 9/2020 | Fabijanski et al. |
| 2020/0288656 | A1 | 9/2020 | Lidor-Nili et al. |
| 2020/0288657 | A1 | 9/2020 | Novirt-Brik et al. |
| 2021/0068335 | A1 | 3/2021 | Noivirt-Brik et al. |
| 2021/0127610 | A1 | 5/2021 | Lidor-Nili et al. |
| 2021/0315176 | A1 | 10/2021 | Shwartz et al. |
| 2024/0057586 | A1 | 2/2024 | Lidor-Nili et al. |
| 2024/0268289 | A1 | 8/2024 | Shwartz et al. |

FOREIGN PATENT DOCUMENTS

| | | |
|---|---|---|
| CN | 1395823 | 2/2003 |
| CN | 101536671 | 9/2009 |
| CN | 102106253 | 6/2011 |
| CN | 103782902 | 5/2014 |
| FR | 2933842 | 1/2010 |
| WO | WO 2014/085774 | 6/2014 |
| WO | WO 2015/164805 | 10/2015 |
| WO | WO 2016/191825 | 12/2016 |
| WO | WO 2017/194399 | 11/2017 |
| WO | WO 2017/203519 | 11/2017 |
| WO | WO 2007/093444 | 7/2018 |
| WO | WO 2019/106666 | 6/2019 |
| WO | WO 2019/106667 | 6/2019 |
| WO | WO 2019/106668 | 6/2019 |
| WO | WO 2019/215581 | 11/2019 |
| WO | WO 2019/215582 | 11/2019 |
| WO | WO 2020/084586 | 4/2020 |
| WO | WO 2020/084586 A9 | 10/2020 |

OTHER PUBLICATIONS

Keller et al. "Genetic introgression from distant provenances reduces fitness in local weed populations". Journal of applied ecology. 37(4): 647-659. (Year: 2001).*
Košmrlj et al. "Haploid Induction in Hull-less Seed Pumpkin through Parthenogenesis Induced by X-ray-irradiated Pollen". Journal of the American Society for Horticultural Science. 138(4): 310-316. (Year: 2013).*
Brewbaker and Emery. Pollen Radiobotany. Radiation Biology. 1: 101-154. (Year: 1961).*
Ward et al. Weed Technology. 27:12-27. (Year: 2013).*
Notification of Office Action Dated Jul. 2, 2021 From the State Intellectual Property Office of the People's Republic of China Re. Application No. 201780037868.0 and Its English Summary. (6 Pages).
Translation Dated Jul. 14, 2021 of Notification of Office Action Dated Jul. 2, 2021 From the State Intellectual Property Office of the People's Republic of China Re. Application No. 200880024068. (6 Pages).
Translation Dated Jul. 14, 2021 of Notification of Office Action Dated Jul. 2, 2021 From the State Intellectual Property Office of the People's Republic of China Re. Application No. 201780037868.0. (6 Pages).
He "Garden Plant Breeding", China Forestry Publishing House: 174-189, Aug. 1992. Chinese Document only).
Communication Pursuant to Article 94(3) EPC Dated Aug. 12, 2021 From the European Patent Office Re. Application No. 17802323.0. (7 Pages).
Restriction Official Action Dated Aug. 2, 2021 Re. U.S. Appl. No. 16/885,311. (8 pages).
Final Official Action Dated Sep. 16, 2021 Re. U.S. Appl. No. 16/304,145. (32 pages).

(Continued)

*Primary Examiner* — Brent T Page
*Assistant Examiner* — David R Byrnes

(57) ABSTRACT

A method of producing pollen that reduces fitness of at least one weed species of interest is provided. The method comprises treating the pollen of plants of a weed species of interest with an irradiation regimen selected from the group consisting of:
(i) X-ray radiation at an irradiation dose of 10-1600 Gy;
(ii) gamma radiation at an irradiation dose of 10-2000 Gy;
(iii) particle radiation; and
(iv) UV-C radiation at an irradiation dose of 100 µJ/cm²-50 J/cm², with the proviso that when said weed is *A. palmeri*, when said irradiation is X-ray, the irradiation dose is not 300 Gy and wherein when said irradiation is gamma irradiation the irradiation dose is not 100, 300 and 500 Gy, and wherein when said radiation is UV-C the dose radiation is not 2 J/cm².

7 Claims, 3 Drawing Sheets
(3 of 3 Drawing Sheet(s) Filed in Color)

(56) References Cited

OTHER PUBLICATIONS

Examination Report Under Sections 12 & 13 of the Patents Act, 1970 and the Patents Rules, 2003 Dated Jul. 16, 2021 From the Government of India, Intellectual Property India, Patents, Designs, Trade Marks, Geographical Indications, The Patent Office Re. Application No. 201827046713. (7 Pages).
Official Action Dated Feb. 17, 2021 Re. U.S. Appl. No. 17/053,089. (45 Pages).
International Preliminary Report on Patentability Dated Jun. 11, 2020 From the International Bureau of WIPO Re. Application No. PCT/IL2018/051301. (8 Pages).
International Preliminary Report on Patentability Dated Jun. 11, 2020 From the International Bureau of WIPO Re. Application No. PCT/IL2018/051302. (7 Pages).
International Preliminary Report on Patentability Dated Jun. 11, 2020 From the International Bureau of WIPO Re. Application No. PCT/IL2018/051303. (8 Pages).
Supplementary European Search Report and the European Search Opinion Dated Aug. 13, 2021 From the European Patent Office Re. Application No. 18883823.9. (8 Pages).
Supplementary European Search Report and the European Search Opinion Dated Aug. 13, 2021 From the European Patent Office Re. Application No. 18883157.2.
International Preliminary Report on Patentability Dated Dec. 6, 2018 From the International Bureau of WIPO Re. Application No. PCT/IL2017/050568. (8 Pages).
International Search Report and the Written Opinion Dated Dec. 12, 2019 From the International Searching Authority Re. Application No. PCT/IB2019/059171. (9 Pages).
International Search Report and the Written Opinion Dated Aug. 14, 2019 From the International Searching Authority Re. Application No. PCT/IB2019/053690. (13 Pages).
International Search Report and the Written Opinion Dated Jul. 14, 2019 From the International Searching Authority Re. Application No. PCT/IB2019/053688. (10 Pages).
International Search Report and the Written Opinion Dated Feb. 21, 2019 From the International Searching Authority Re. Application No. PCT/IL2018/051301. (11 Pages).
International Search Report and the Written Opinion Dated Aug. 23, 2017 From the International Searching Authority Re. Application No. PCT/IL2017/050568. (11 Pages).
International Search Report and the Written Opinion Dated Feb. 24, 2019 From the International Searching Authority Re. Application No. PCT/IL2018/051302. (9 Pages).
International Search Report and the Written Opinion Dated Feb. 26, 2019 From the International Searching Authority Re. Application No. PCT/IL2018/051303. (11 Pages).
Office Action Dated Jul. 9, 2019 From the Israel Patent Office Re. Application No. 263232 and Its Translation Into English. (5 Pages).
Supplementary European Search Report and the European Search Opinion Dated Oct. 25, 2019 From the European Patent Office Re. Application No. 17802323.0. (9 Pages).
Al-Ahmad et al. "Mitigation of Establishment of *Brassica napus* Transgenes in Volunteers Using a Tandem Construct Containing a Selectively Unfit Gene", Plant Biotechnology Journal, XP055444715, 4(1): 7-21, Jan. 2006. Abstract, p. 16, r-h col. 1st Para, p. 17, l-h col. 4th Para.
Al-Ahmad et al. "Mitigation Using a Tandem Construct Containing a Selectively Unfit Gene Precludes Establishment of *Brassica napus* Transgenes in Hybrids and Backcrosses With Weedy *Brassica rapa*", Plant Biotechnology Journal, XP055444720, 4(1): 23-33, Published Online Aug. 16, 2005. Abstract, Table S2, p. 31, l-h col. Lines 10-11, 18-23.
Chin et al. "Pollination With Irradiated Pollen in Rice—*Oryza sativa* L. I. First (M1) Generation", Heredity, 63(2): 163-170, Published Online Oct. 1, 1989.

Germana "Use of Irradiated Pollen to Induce Parthenogenesis and Haploid Production in Fruit Crops", Plant Mutation Breeding and Biotechnology, XP009516584, p. 411-415, Published Online Dec. 31, 2012.
Gressel et al. "A Strategy to Provide Long-Term Control of Weedy Rice While Mitigating Herbicide Resistance Transgene Flow, and Its Potential Use for Other Crops With Related Weeds", Pest Management Science, XP055053395, 65(7): 723-731, Published Online Apr. 14, 2009.
Jordan et al. "Biorational Management Tactics to Select Against Triazine-Resistant Amaranthus Hybridus: A Field Trial", Journal of Applied Ecology, 36(1): 123-132, Feb. 1999.
Keller et al. "Genetic Introgression From Distant Provenances Reduces Fitness in Local Weed Populations", Journal of Applied Ecology, 37(4): 647-659, Aug. 2000.
Kurtar "Influence of Gamma Irradiation on Pollen Viability, Germination Ability, and Fruit and Seed-Set of Pumpkin and Winter Squash", African Journal of Biotechnology, 8(24): 6918-6926, Dec. 15, 2009.
Kwit et al. "Transgene Introgression in Crop Relatives: Molecular Evidence and Mitigation Strategies", Trends in Biotechnology, XP002794936, 29(6): 284-293, Published Online Mar. 8, 2011.
Lagera et al. "Varying Sugars and Sugar Concentrations Influence In Vitro Pollen Germination and Pollen Tube Growth of *Cassia alata* L.", Journal of Young Investigations, 33(1): 42-45, Jun. 2017.
Li et al. "Effects of Sowing Date on Phenotypic Plasticity of Fitness-Related Traits in Two Annual Weeds on the Songnen Plain of China", PLOS ONE, 10(5): e0127795-1-0127795-15, May 29, 2005.
Ma "Why Don't They Genetically Modify Weeds Instead fo Crops? Wouldn't It Make More Sense to Genetically Alter Species of Weeds to Become Interfile After a Few Generations, Thereby Reducing the Need for Herbicides?", Quora.com, 1 P., Apr. 2, 2014.
Munusamy et al. "Female Reproductive System of Amaranthus as the Target for Agrobacterium-Mediated Transformation", Advances in Biscience and Biotechnology, 4(2): 188-192, Published Online Feb. 28, 2013.
Peixe et al. "Gamma-Irradiated Pollen Induces the Formation of 2n Endosperm and Abnormal Embryo Development in European Plum (*Prunus domestica* L., Cv. 'Rainha Claudia Verde')", Scientia Horticulturae, 86(4): 267-278, Dec. 2000.
Shu "Use of Irradiated Pollen to Induce Pathogenesis and Haploid Production in Fruit Crops", Plant Mutation Breeding and Biotechnology, C30: 412-416, Dec. 2012.
Yang et al. "Molecular Genetic Analysis of Pollen Irradiation Mutagenesis in *Arabidopsis*", New Phytologist, XP055615348, 164(2): 279-288, Published Online Sep. 10, 2004.
Official Action Dated Dec. 30, 2020 Re. U.S. Appl. No. 16/304,145. (37 pages).
Bae et al. "Production of Unbolting Lines Through Gamma-Ray Irradiation Mutagenesis in Genetically Modified Herbicide-Tolerant *Zoysia japonica*", Breeding Science, 59(1): 103-105, 2009.
International Preliminary Report on Patentability Dated May 6, 2021 From the International Bureau of WIPO Re. Application No. PCT/IB2019/059171. (7 Pages).
Final Official Action Dated Jul. 21, 2021 Re. U.S. Appl. No. 17/053,089. (34 pages).
Communication Pursuant to Article 94(3) EPC Dated Nov. 20, 2020 From the European Patent Office Re. Application No. 17802323.0. (5 Pages).
International Preliminary Report on Patentability Dated Nov. 19, 2020 From the International Bureau of WIPO Re. Application No. PCT/IB2019/053688. (7 Pages).
Official Action Dated Feb. 2, 2021 Re. U.S. Appl. No. 16/884,097. (36 Pages).
Culpepper et al. "Glyphosate-Resistant Palmer Amaranth (*Amaranthus palmeri*) Confirmed in Georgia", Weed Science, 54(4):620-626, Jul. 1, 2006.
Daher et al. "Optimization of Conditions for Germination of Cold-Stored *Arabidopsis thaliana* Pollen", Plant Cell Reports, 28: 347-357, 2009.

(56) References Cited

OTHER PUBLICATIONS

Preston et al. "A Decade of Glyphosate-Resistant Lolium around the World: Mechanisms, Genes, Fitness, and Agronomic Management", Weed Science, 57(4):435-441, Jul. 1, 2009.
Tacconi et al. "Kiwifruit Pollination: the Interaction Between Pollen Quality, Pollination Systems and Flowering Stage", Journal of Berry Research, 6(4): 417-426, Dec. 12, 2016.
Office Action Dated Dec. 10, 2020 From the Israel Patent Office Re. Application No. 263232 and Its Translation Into English. (9 Pages).
Restriction Official Action Dated Oct. 1, 2020 Re. U.S. Appl. No. 16/304,145. (9 pages).
Final Official Action Dated Nov. 3, 2021 Re. U.S. Appl. No. 16/884,097. (36 pages).
Official Action Dated Nov. 18, 2021 Re. U.S. Appl. No. 16/885,311. (55 pages).
Interview Summary Dated Dec. 13, 2021 Re. U.S. Appl. No. 16/304,145. (2 pages).
English Translation of Notification of Office Action Dated Jan. 25, 2022 From the State Intellectual Property Office of the People's Republic of China Re. Application No. 201780037868.0. (5 Pages).
Notification of Office Action and Search Report Dated Mar. 10, 2022 From the State Intellectual Property Office of the People's Republic of China Re. Application No. 201880086827.5. (25).
Restriction Official Action Dated May 3, 2022 Re. U.S. Appl. No. 17/052,834. (6 pages).
Notice of Allowance Dated Feb. 9, 2022 Re. U.S. Appl. No. 16/304,145. (7 pages).
English Translation Dated Apr. 6, 2022 of Notification of Office Action and Search Report Dated Mar. 10, 2022 From the State Intellectual Property Office of the People's Republic of China Re. Application No. 201880086827.5. (4 Pages).
Office Action Dated Mar. 31, 2022 From the Israel Patent Office Re. Application No. 263232 and Its Translation Into English. (6 Pages).
Notice of Allowance Dated Dec. 21, 2021 Re. U.S. Appl. No. 17/053,089. (12 pages).
Advisory Action Dated Mar. 1, 2022 Re. U.S. Appl. No. 16/884,097. (11 Pages).
Murphy "The Role of Pollen Allelopathy in Weed Ecology", Weed Technology, 15(4):867-872, Dec. 2001.
Official Action Dated Sep. 9, 2022 Re. U.S. Appl. No. 17/052,834. (65 pages).
Relatório de Busca e Parecer [Search Report and Written Opinion] Dated Sep. 19, 2022 From the Serviço Público Federal, Ministério da Economia, Instituto Nacional da Propriedade Industrial do Brasil Re. Application No. BR112018074045-4 and Its Summary of Written Opinion in English. (6 Pages).
Restriction Official Action Dated Nov. 15, 2022 Re. U.S. Appl. No. 17/287,574. (14 pages).
Yang et al. "Molecular Genetic analysis of Pollen Irradiation Mutagenesis in *Arabidopsis*", New Phytologist, 164(2): 279-288, Sep. 10, 2004.
Communication Pursuant to Article 94(3) EPC Dated Dec. 2, 2022 From the European Patent Office Re. Application No. 17802323.0 with Claims. (7 Pages).
Examination Report Dated Jan. 27, 2023 From the Australian Government, IP Australia Re. Application No. 2017271409. (5 Pages).
Notification of Office Action Dated Jan. 9, 2023 From the State Intellectual Property Office of the People's Republic of China Re. Application No. 201780037868.0. (4 Pages).
Notification of Office Action Dated Dec. 28, 2022 From the China National Intellectual Property Administration Re. Application No. 201880086827.5. (5 Pages).
Translation Dated Jan. 13, 2023 of Notification of Office Action Dated Dec. 28, 2022 From the China National Property Administration Re. Application No. 201880086827.5. (3 Pages).
Translation Dated Jan. 19, 2023 of Notification of Office Action Dated Jan. 9, 2023 From the State Intellectual Property Office of the People's Republic of China Re. Application No. 201780037868.0. (6 Pages).
Decision on Rejection Dated May 29, 2023 From the State Intellectual Property Office of the People's Republic of China Re. Application No. 201880086827.5. (4 Pages).
Communication Pursuant to Article 94(3) EPC Dated Jul. 20, 2023 From the European Patent Office Re. Application No. 18883157.2 (5 Pages).
Final Official Action Dated Jun. 30, 2022 Re. U.S. Appl. No. 16/885,311. (30 pages).
Notification of Office Action Dated Jun. 24, 2022 From the State Intellectual Property Office of the People's Republic of China Re. Application No. 201780037868.0 and Its Translation Into English. (10 Pages).
Office Action Dated Feb. 28, 2023 From the Israel Patent Office Re. Application No. 274978. (3 Pages).
Official Action Dated Feb. 9, 2023 Re. U.S. Appl. No. 17/052,834. (25 pages).
Andreichenko et al. "Possibility of Regulating Seed Formation During Pollination with Mixed Pollen Containing γ-irradiated Pollen", A. A. Bogomolets Kiev Medical Institute, Kiev, Doklady, Biological Sciences, 315(1-6): 699-702, ref.15, Dec. 1990.
Feng et al. "Effect of Enhanced Ultraviolet-B Radiation on Pollen Germination and Tube Growth of 19 Taxa in Vitro", Environmental and Experimental Botany, 43(1):45-53, Feb. 2000.
Hansen "Precision Pollination. Mechanical Pollination Could end Use of Chemicals or Hand Labor for Thinning." Retrieved from the Internet: www.goodfruit.com, 4 pages, Mar. 18, 2015.
Requisition by the Examiner Dated Jun. 9, 2023 From the Innovation, Science and Economic Development Canada, Canadian Intellectual Property Office Re. Application No. 3,024,079. (6 Pages).
Translation Dated Jun. 17, 2023 of Decision on Rejection Dated May 29, 2023 From the State Intellectual Property Office of the People's Republic of China Re. Application No. 201880086827.5. (3 pages).
Official Action Dated May 24, 2023 Re. U.S. Appl. No. 17/287,574. (106 Pages).
Marcelis et al. "Flower and Fruit Abortion in Sweet Pepper in Relation to Source and Sink Strength", Journal of Experimental Botany, 55(406): 2261-2268, Oct. 2004.
Muthoni et al. "Reproductive Biology and Early Generation's Selection in Conventional Potato Breeding", Australian Journal of Crop Science, 6(3): 488-497, Mar. 2012.
Ribeiro et al. "Involvement of Facultative Apomixis in Inheritance of EPSPS Gene Amplification in Glyphosate-resistant *Amaranthus palmeri*", Planta, 239: 199-212, 2014.
Spaunhorst et al. "Phenology of Five Palmer Amaranth (*Amaranthus palmeri*) Populations Grown in Northern Indiana and Arkansas", Weed Science 66(4): 457-469, Mar. 27, 2018.
Notice of Allowance Dated Dec. 13, 2023 Re. U.S. Appl. No. 17/287,574. (17 pages).
Official Action Dated Dec. 7, 2023 Re. U.S. Appl. No. 16/885,311. (23 pages).
Official Action Dated Apr. 30, 2024 Re. U.S. Appl. No. 18/385,412. (25 pages).
Communication Pursuant to Article 94(3) EPC Dated Aug. 28, 2024 From the European Patent Office Re. Application No. 17802323.0. (4 Pages).
Notice of Allowance Dated Aug. 30, 2024 Re. U.S. Appl. No. 18/385,412. (9 pages).
Requisition by the Examiner Dated Sep. 5, 2024 From the Innovation, Science and Economic Development Canada Re. Application No. 3,024,079. (3 Pages).
Communication Pursuant to Article 94(3) EPC Dated Sep. 25, 2024 From the European Patent Office Re. Application No. 18883157.2 (5 Pages).
Requisition by the Examiner Dated May 22, 2024 From the Innovation, Science and Economic Development Canada, Canadian Intellectual Property Office Re. Application No. 3,100,078. (3 Pages).
Notification of Office Action Dated Jan. 25, 2022 From the State Intellectual Property Office of the People's Republic of China Re. Application No. 201780037868.0 with an English Summry. (6 Pages).

(56) References Cited

OTHER PUBLICATIONS

Clarifications Prior to Substantive Examination Dated Nov. 18, 2021 From the Instituto Nacional De La Propiedad Industrial Administracion Nacional De Patentes Argentina Re. Applicatiion No. P20170101373 together with English Summary. (6 Pages).

* cited by examiner

COMPOSITIONS, KITS AND METHODS FOR CONTROLLING WEED

RELATED APPLICATIONS

This application is a Continuation of PCT Patent Application No. PCT/IL2018/051301 having international filing date of Nov. 28, 2018, which claims the benefit of priority under 35 USC § 119(e) of U.S. Provisional Patent Application No. 62/591,801 filed on Nov. 29, 2017. The contents of the above applications are all incorporated by reference as if fully set forth herein in their entirety.

FIELD AND BACKGROUND OF THE INVENTION

The present invention, in some embodiments thereof, relates to compositions, kits and methods for controlling weed.

Weeds have been the major biotic cause of crop yield loses since the origins of agriculture. The potential of weed damages is estimated as 34% loss of crop yield, on average, world-wide [Oerke, E-C., 2006]. In the USA alone, the annual cost of crop losses due to weeds is greater than 26 billion USD [Pimentel D et al., 2000]. Furthermore according to the Weed Science Society of America Weeds are estimated to cause more than 40 billion USD in annual global losses [wssa(dot)net/wssa/weed/biological-control/]. Weeds are thus a major threat to food security [Delye et al., 2013].

Herbicides are the most commonly used and effective weed control tools. Due to the intense selection pressure exerted by herbicides, herbicide resistance is constantly growing and as of 2016 there are over 470 weed biotypes currently identified as being herbicide resistant to one or more herbicides by The International Survey of Herbicide Resistant Weeds (weedscience(dot)org/).

Weeds, like other plants, have several sexual reproduction mechanisms: self-pollination, cross-pollination, or both. Self-pollination describes pollination using pollen from one flower that is transferred to the same or another flower of the same plant. Cross-pollination describes pollination using pollen delivered from a flower of a different plant. Weeds rely on wind, or animals such as bees and other insects to pollinate them.

Since the 1940's the use of sterile organisms has been reported for use in order to reduce pest population and the success of these methods was demonstrated in many cases such as the tsetse fly [Klassen& Curtis, 2005], melon fly [Yosiaki et al. 2003] and Sweet potato weevil [Kohama et al., 2003].

Planting in the field plants producing sterile pollen for the production of infertile seeds was mentioned but immediately over-ruled due to practical, regulatory and economic reasons. (quora(dot)com/Why-dont-they-genetically-modify-weeds-instead-of-crops).

Therefore, there still exists a need for biological weed control.

SUMMARY OF THE INVENTION

According to an aspect of some embodiments of the present invention there is provided a method of producing pollen that reduces fitness of at least one weed species of interest, the method comprising treating the pollen of plants of a weed species of interest with an irradiation regimen selected from the group consisting of:

(i) X-ray radiation at an irradiation dose of 10-1600 Gy;
(ii) gamma radiation at an irradiation dose of 10-2000 Gy;
(iii) particle radiation; and
(iv) UV-C radiation at an irradiation dose of 100 J/cm$^2$-50 J/cm$^2$, with the proviso that when the weed is *A. palmeri*, when the irradiation is X-ray, the irradiation dose is not 300 Gy and wherein when the irradiation is gamma irradiation the irradiation dose is not 100, 300 and 500 Gy, and wherein when the radiation is UV-C the dose radiation is not 2 J/cm$^2$.

According to some embodiments of the invention, the particle radiation dose at an irradiation dose of 20-5000 Gy.

According to some embodiments of the invention, the pollen is a harvested pollen.

According to some embodiments of the invention, the pollen is a non-harvested pollen.

According to some embodiments of the invention, the method further comprises harvesting the pollen following the treating.

According to some embodiments of the invention, the weed species of interest comprise only male plants.

According to some embodiments of the invention, the plants are grown in a large scale setting.

According to some embodiments of the invention, the large-scale setting essentially does not comprise crops.

According to an aspect of some embodiments of the present invention there is provided harvested pollen obtainable according to the method as described herein.

According to an aspect of some embodiments of the present invention there is provided a method of weed control, the method comprising artificially pollinating a weed species of interest with the pollen as described herein.

According to some embodiments of the invention, the pollen and the weed species of interest are of the same species.

According to some embodiments of the invention, the pollen and the weed species of interest are of different species.

According to some embodiments of the invention, the artificially pollinating is effected in a large scale setting.

According to some embodiments of the invention, the pollen is herbicide resistant.

According to some embodiments of the invention, the pollen is coated with the herbicide.

According to some embodiments of the invention, the artificially pollinating results in reduced average seed weight of at least 1.2 lower than that of the average seed weight of a plant of the same developmental stage and of the same species fertilized by control pollen.

According to an aspect of some embodiments of the present invention there is provided a method of producing pollen for use in artificial pollination, the method comprising:

(a) providing the pollen as described herein; and
(b) treating the pollen for use in artificial pollination.

According to an aspect of some embodiments of the present invention there is provided a composition-of-matter comprising the pollen as described herein, the pollen having been treated for use in artificial pollination.

According to an aspect of some embodiments of the present invention there is provided a kit comprising a plurality of packaging means, each packaging different species of pollen wherein at least one of the different species of pollen is the pollen as described herein or the treated pollen.

According to some embodiments of the invention, a treatment of the treated pollen is selected from the group consisting of coating, priming, formulating, solvent solubilizing, chemical treatment, drying, heating, cooling and irradiating.

According to some embodiments of the invention, the weed species of interest is selected from the group consisting of a biotic stress or abiotic stress resistant weed.

According to some embodiments of the invention, the Weed species of interest is a herbicide resistant weed.

According to some embodiments of the invention, the pollen is of an herbicide susceptible weed.

According to some embodiments of the invention, the herbicide susceptible weed is susceptible to a plurality of herbicides.

According to some embodiments of the invention, the pollen reduces productiveness of the weed species of interest.

According to some embodiments of the invention, reduction in the productiveness is manifested by:

(i) inability to develop an embryo;
(ii) embryo abortion;
(iii) seed non-viability;
(iv) seed that cannot fully develop;
(v) seed that is unable to germinate; and/or
(vi) reduced or no seed set.

According to some embodiments of the invention, the pollen is non-genetically modified pollen.

According to some embodiments of the invention, the non-genetically modified pollen is produced from a plant having an imbalanced chromosome number.

According to some embodiments of the invention, the pollen is genetically modified pollen.

According to some embodiments of the invention, the composition or kit further comprises at least one agent selected from the group consisting of an agricultural acceptable carrier, a fertilizer, a herbicide, an insecticide, a miticide, a fungicide, a pesticide, a growth regulator, a chemosterilant, a semiochemical, a pheromone and a feeding stimulant.

According to some embodiments of the invention, the at least one weed species of interest comprises a plurality of weed species of interest.

According to some embodiments of the invention, the irradiation is X-ray with an irradiation dose of 20-500 Gy.

According to some embodiments of the invention, the irradiation is gamma irradiation with an irradiation dose of 20-1200 Gy.

According to some embodiments of the invention, the irradiation is UV-C irradiation with an irradiation dose of 1 mJ/cm$^2$-10 J/cm$^2$.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a graph showing that the weight of seed obtained by artificial pollination is equivalent to that of seeds collected from the field or obtained by natural pollination.

FIG. 2 is an image showing inhibition of seed development demonstrated by comparing the appearance of random assortment of seeds generated by artificial pollination with X-ray irradiated pollen vs. non-irradiated pollen.

FIG. 3 is an image showing inhibition of seed development demonstrated by comparing the appearance of random assortment of seeds generated by artificial pollination with X-ray irradiated pollen vs. non-irradiated pollen.

FIG. 4 is an image showing inhibition of seed development demonstrated by comparing the appearance of random assortment of seeds generated by artificial pollination with gamma irradiated pollen vs. non-irradiated pollen. A dose response is demonstrated.

Figure 5:
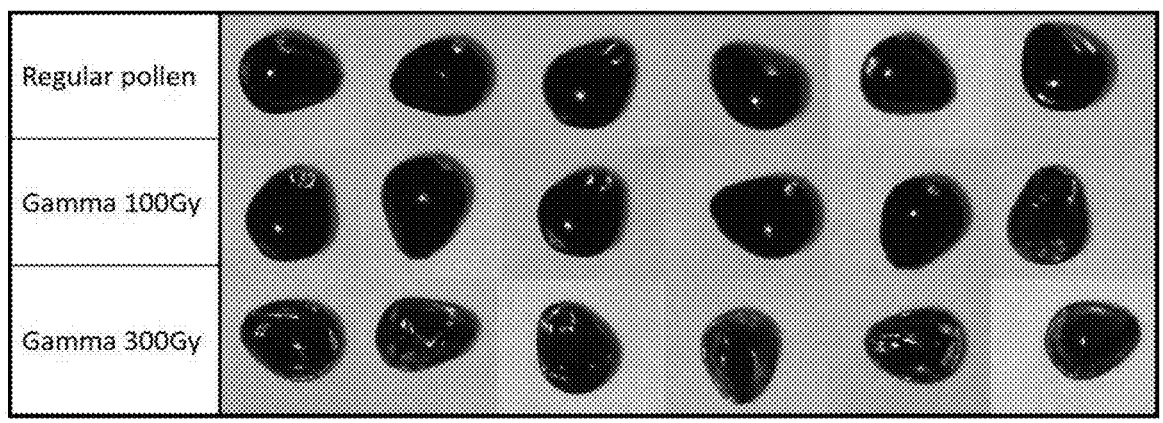

FIG. 5 an image showing inhibition of seed development demonstrated by comparing the appearance of random assortment of seeds generated by artificial pollination with gamma irradiated pollen vs. non-irradiated pollen. A dose response is demonstrated.

DESCRIPTION OF SPECIFIC EMBODIMENTS OF THE INVENTION

The present invention, in some embodiments thereof, relates to compositions, kits and methods for controlling weed.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Weeds are plants that are unwanted in any particular environment. They compete with cultivated plants in an agronomic environment and also serve as hosts for crop diseases and insect pests. The losses caused by weeds in agricultural production environments include decreases in crop yield, reduced crop quality, increased irrigation costs, increased harvesting costs, reduced land value, injury to livestock, and crop damage from insects and diseases harbored by the weeds.

The use of herbicides and other chemicals to control weed has generated environmental concern.

Whilst conceiving the present invention, the present inventors have devised a novel approach for the biological control of weeds. The approach is based on producing weed pollen that when artificially applied to the invasive weed out-competes with native fertilization and causes reduction in fitness of the weed. Thus, the present teachings provide for products and methods which are highly efficient, environmentally safe and that can be successfully applied as a practical and economically affordable weed control in plethora of settings.

Thus, according to an aspect of the invention there is provided a method of weed control. The method comprises artificially pollinating at least one weed species of interest with pollen of the same species that reduces fitness of the at least one weed species of interest.

As used herein the term "weed species of interest" refers to a wild plant growing where it is not wanted and that may be in competition with cultivated plants of interest (i.e., crop-desirable plants). Weeds are typically characterized by rapid growth and/or ease of germination, and/or competition with crops for space, light, water and nutrients. According to some embodiments of the invention, the weed species of interest is traditionally non-cultivated.

As used herein the term "weed species of interest" refers to a wild plant growing where it is not wanted and that may be in competition with cultivated plants of interest (i.e., crop-desirable plants). Weeds are typically characterized by rapid growth and/or ease of germination, and/or competition with crops for space, light, water and nutrients. According to some embodiments of the invention, the weed species of interest is traditionally non-cultivated.

According to another embodiment of the invention, the weed is a perennial weed.

According to another embodiment of the invention the weed is a biennial weed.

According to another embodiment of the invention the weed is an annual weed.

According to another embodiment of the invention the weed is a therophyte.

According to an embodiment, the weed is a parasitic plant.

Examples of weed species which can be targeted (mitigated) according to the present teachings include, but are not limited to, *Amaranthus* species—*A. albus, A. blitoides, A. hybridus, A. palmeri, A. powellii, A. retroflexus, A. rudis, A. spinosus, A. tuberculatus, A. thunbergii, A. graecizans* and *A. viridis*; *Ambrosia* species—*A. trifida, A. artemisifolia*; *Lolium* species—*L. multiflorum, L. rigidium, L perenne*; *Digitaria* species—*D. insularis, D. sanguinalis*; *Euphorbia* species—*E. heterophylla*; *Kochia* species—*K. scoparia*; *Sorghum* species—*S. halepense*; *Conyza* species—*C. bonariensis, C. canadensis, C. sumatrensis*; *Chloris* species—*C. truncate*; *Echinochola* species—*E. colona, E. crus-galli*; *Eleusine* species—*E. indica*; *Poa* species—*P. annua*; *Plantago* species—*P. lanceolata*; *Avena* species—*A. fatua*; *Chenopodium* species—*C. album*; *Setaria* species—*S. viridis*, *Abutilon theophrasti, Ipomoea* species, *Sesbania*, species, *Xanthium strumarium, Cassia* species, *Sida* species, *Brachiaria* species, *Sporobolus* species—*S. pyramidalis, S. natalensis, S. jacquemontii, S. fertilis, S. africanus S. indicus, Solanum nigrum, Solanum carolinense*, and *Solanum elaeagnifolium*.

Additional weedy plant species found in cultivated areas include *Alopecurus myosuroides, Avena sterilis, Avena sterilis ludoviciana, Brachiaria plantaginea, Bromus diandrus, Bromus rigidus, Cynosurus echinatus, Digitaria ciliaris, Digitaria ischaemum, Digitaria sanguinalis, Echinochloa oryzicola, Echinochloa phyllopogon, Eriochloa punctata, Hordeum glaucum, Hordeum leporinum, Ischaemum rugosum, Leptochloa chinensis, Lolium persicum, Phalaris minor, Phalaris paradoxa, Rottboellia exalta, Setaria faberi, Setaria viridisvar, robusta-alba schreiber, Setaria viridisvar, robusta-purpurea, Snowdenia polystachea, Sorghum sudanese, Alisma plantago-aquatica, Amaranthus lividus, Ammaniaauriculata, Ammania coccinea, Anthemis cotula, Apera spica-venti, Bacopa rotundifolia, Bidens pilosa, Bidens subalternans, Brassica tournefortii, Bromus tectorum, Camelina microcarpa, Chrysanthemum coronarium, Cuscuta campestris, Cyperus difformis, Damasonium minus, Descurainia sophia, Diplotaxis tenuifolia, Echium plantagineum, Elatine triandravar, pedicellata, Euphorbia heterophylla, Fallopia convolvulus, Fimbristylis miliacea, Galeopsis tetrahit, Galium spurium, Helianthus annuus, Iva xanthifolia, Ixophorusunisetus, Ipomoea indica, Ipomoea purpurea, Ipomoea sepiaria, Ipomoea aquatic, Ipomoea triloba, Lactuca serriola, Limnocharis flava, Limnophila erecta, Limnophila sessiliflora, Lindernia dubia, Lindernia dubiavar, major, Lindernia micrantha, Lindemia procumbens, Mesembryanthemum crystallinum, Monochoria korsakowii, Monochoria vaginalis, Neslia paniculata, Papaver rhoeas, Parthenium hysterophorus, Pentzia suj fruticosa, Phalaris minor, Raphanus raphanistrum, Raphanus sativus, Rapistrum rugosum, Rotalaindicavar, uliginosa, Sagittaria guyanensis, Sagittaria montevidensis, Sagittaria pygmaea, Salsola iberica, Scirpus juncoidesvar, ohwianus, Scirpus mucronatus, Setaria lutescens, Sida spinosa, Sinapis arvensis, Sisymbrium orientale, Sisymbrium thellungii, Solanum ptycanthum, Sonchus asper, Sonchus oleraceus, Sorghum bicolor, Stellaria media, Thlaspi arvense, Xanthium strumarium, Arctotheca calendula, Conyza sumatrensis, Crassocephalum crepidiodes, Cuphea carthagenenis, Epilobium adenocaulon, Erigeron philadelphicus, Landoltia punctata, Lepidium virginicum, Monochoria korsakowii, Solanum americanum, Solanum nigrum, Vulpia bromoides, Youngia japonica, Hydrilla verticillata, Carduus nutans, Carduus pycnocephalus, Centaurea solstitialis, Cirsium arvense, Commelina diffusa, Convolvulus arvensis, Daucuscarota, Digitaria ischaemum, Echinochloa crus-pavonis, Fimbristylis miliacea, Galeopsis tetrahit, Galium spurium, Limnophila erecta, Matricaria perforate, Papaver rhoeas, Ranunculus acris, Soliva sessilis, Sphenoclea zeylanica, Stellaria media, Nassella trichotoma, Stipa neesiana, Agrostis stolonifera, Polygonum aviculare, Alopecurus japonicus, Beckmannia syzigachne, Bromus tectorum, Chloris inflate, Echinochloa erecta, Portulaca oleracea*, and *Senecio vulgaris*.

According to a specific embodiment the weed species is selected from or belong to the group consisting of *Amaranthus: A. palmeri, A. tuberculatus A. retroflexus, Lolium rigidum, Lolium multiflorum, Lolium perenne, Ambrosia: A. trifida, A. artemisiifolia, Kochia scoparia, Conyza: C. canadensis, C. bonariensis, Echinochloa: E. crus galli, E colona, Alopecurus myosuroides, Sorghum halepense, Digitaria: D. insularis D. sanguinalis, Eleusine indica, Avena: A. fatua, A. sterilis, A. spinosus, Euphorbia Heterophylla, Chenopodium album*.

According to an embodiment, the weed is a parasitic plant. Examples of parasitic plants include, but are not limited to, *Striga* sp, *Orobanche* sp, *Cuscuta* sp, Mistletoe.

Different weed may have different growth habits and therefore specific weeds usually characterize a certain crop in given growth conditions.

According to a specific embodiment, the weed is a herbicide resistant weed.

According to a specific embodiment, weed is defined as herbicide resistant when it meets the Weed Science Society of America (WSSA) definition of resistance.

Accordingly, WSSA defines herbicide resistance as "the inherited ability of a plant to survive and reproduce following exposure to a dose of herbicide normally lethal to the wild type. Alternatively, herbicide resistance is defined as "The evolved capacity of a previously herbicide-susceptible weed population to withstand an herbicide and complete its life cycle when the herbicide is used at its normal rate in an agricultural situation" (Source: Heap and Lebaron. 2001 in Herbicide Resistance and World Grains).

As used herein the phrase "weed control" refers to suppressing growth and optionally spread of a population of at least one weed species of interest and even reducing the size of the population in a given growth area.

According to a specific embodiment, the growth area is an urban area, e.g., golf courses, athletic fields, parks, cemeteries, roadsides, home gardens/lawns and the like.

According to an additional or alternative embodiment, the growth area is a rural area.

According to an additional or an alternative embodiment, the growth area is an agricultural growth area e.g., open field, greenhouse, plantation, vineyard, orchard and the like.

As mentioned, weed control according to the present teachings is effected by reducing fitness of the at least one weed species of interest.

As used herein "fitness" refers to the relative ability of the weed species of interest to develop, reproduce or propagate and transmit its genes to the next generation. As used herein "relative" means in comparison to a weed of the same species not having been artificially pollinated with the pollen of the invention and grown under the same conditions.

It will be appreciated that the effect of pollen treatment according to the present teachings is typically manifested in the first generation after fertilization.

The fitness may be affected by reduction in productiveness, propagation, fertility, fecundity, biomass, biotic stress tolerance, abiotic stress tolerance and/or herbicide resistance.

As used herein "productivity" refers to the potential rate of incorporation or generation of energy or organic matter by an individual, population or trophic unit per unit time per unit area or volume; rate of carbon fixation.

As used herein "fecundity" refers to the potential reproductive capacity of an organism or population, measured by the number of gametes.

According to a specific embodiment, the pollen affects any stage of seed development or germination.

According to a specific embodiment, the reduction in productiveness is manifested by at least one of:
 (i) inability to develop an embryo;
 (ii) embryo abortion;
 (iii) seed non-viability;
 (iv) seed that cannot fully develop; and/or
 (v) seed that is unable to germinate (e.g., reduced germination by at least 70%, 80%, 85%, 90%, or even 100% as compared to seed produced from a control plant that was not subjected to fertilization by the pollen of the invention); and/or
 (vi) reduced or no seed set.

It will be appreciated that when pollen reduces the productiveness, fertility, propagation ability or fecundity of the weed in the next generation it may be referred to by the skilled artisan as sterile pollen, though it fertilizes the weed of interest. Hence, sterile pollen as used herein is still able to fertilize but typically leads to seed developmental arrest or seed abortion.

According to a specific embodiment, the reduction in fitness is by at least 10%, 20%, 30%, 40%, 50%, 60%, 70%, 75%, 80%, 85%, 90%, 92%, 95%, 97% or even 100%, within first generation after fertilization, and optionally second generation after fertilization and optionally third generation after fertilization.

According to a specific embodiment, the reduction in fitness is by at least 10%, 20%, 30%, 40%, 50%, 60%, 70%, 75%, 80%, 85%, 90%, 92%, 95%, 97% or even 100%, within first generation after fertilization.

According to a specific embodiment, reduced fitness results from reduction in tolerance to biotic or abiotic conditions e.g., herbicide resistance.

Non-limiting examples of abiotic stress conditions include, salinity, osmotic stress, drought, water deprivation, excess of water (e.g., flood, waterlogging), etiolation, low temperature (e.g., cold stress), high temperature, heavy metal toxicity, anaerobiosis, nutrient deficiency (e.g., nitrogen deficiency or nitrogen limitation), nutrient excess, atmospheric pollution, herbicide, pesticide and UV irradiation.

Biotic stress is stress that occurs as a result of damage done to plants by other living organisms, such as bacteria, viruses, fungi, parasites, beneficial and harmful insects, weeds, and cultivated or native plants.

Examples of herbicides which are contemplated according to the present teachings, include, but are not limited to, ACCase inhibitors, ALS inhibitors, Photosystem II inhibitors, PSII inhibitor (Ureas and amides), PSII inhibitors (Nitriles), PSI Electron Diverter, PPO inhibitors, Carotenoid biosynthesis inhibitors, HPPD inhibitors, Carotenoid biosynthesis (unknown target), EPSP synthase inhibitors, Glutamine synthase inhibitors, DHP synthase inhibitors, Microtubule inhibitors, Mitosis inhibitors, Long chain fatty acid inhibitors, Cellulose inhibitors, Uncouplers, Lipid Inhibitors (thiocarbamates), Synthetic Auxins, Auxin transport inhibitors, Cell elongation inhibitors, Antimicrotubule mitotic disrupter, Nucleic acid inhibitors or any other form of herbicide site of action.

As used herein "pollen" refers to pollen that is able to fertilize the weed species of interest and therefore competes with native pollination.

Alternatively, when native pollen competition does not exist, or very low levels of native pollen are present, pollination by the designed pollen inhibits apomixis of weeds and by this reduces their quantities as well [Ribeiro et al. 2012].

According to a specific embodiment, the pollen is of the same species as of the target weed (e.g., invasive, aggressive weed).

According to a specific embodiment, the pollen exhibits susceptibility to a single growth condition e.g., herbicide, temperature.

According to a specific embodiment, the pollen exhibits susceptibility to multiple growth conditions e.g., different herbicides (see Example 9).

According to a specific embodiment, the pollen is non-genetically modified.

According to a specific embodiment, there is provided a method of producing pollen that reduces fitness of at least one weed species of interest, the method comprising treating the weed species of interest (e.g., seeds, seedlings, tissue/cells) or pollen thereof with an agent that reduces fitness.

When needed (such as when treating that weed (e.g., seeds, seedlings, tissue/cells) the method further comprises growing or regenerating the plant so as to produce pollen.

According to a specific embodiment, the method comprises harvesting pollen from the weed species of interest following treating with the agent that reduces the fitness.

It will be appreciated that the pollen may be first harvested and then treated with the agent (e.g., radiation) that reduces the fitness of the weed species of interest.

According to a specific embodiment, treatment of the pollen is with an irradiation regimen selected from the group consisting of:

(i) X-ray irradiation at an irradiation dose of 10-1600 Gy. Examples include but are not limited to, 20-1000 Gy, 20-900 Gy, 20-800 Gy, 20-700 Gy, 20-600 Gy, 20-500 Gy, 20-400 Gy, 20-300 Gy, 20-200 Gy, 20-100 Gy, 50-1600 Gy, 50-1400 Gy, 50-1200 Gy, 50-1000 Gy, 50-900 Gy, 50-800 Gy, 50-700 Gy, 50-600 Gy, 50-550 Gy, 50-500 Gy, 50-400 Gy, 50-350 Gy, 50-300 Gy, 50-200 Gy, 50-150 Gy, 50-100 Gy, 100-1600 Gy, 100-1500 Gy, 100-1400 Gy, 100-1300 Gy, 100-800 1200, 100-1000 Gy, 100-900 Gy, 100-800 Gy, 100-700 Gy, 100-600 Gy, 100-500 Gy, 100-400 Gy, 100-300 Gy, 100-200 Gy, 300-800 Gy, 300-700 Gy, 300-500 Gy, 50-600 Gy, 50-500 Gy, 50-400 Gy, 50-300 Gy, 50-200 Gy, 500-800 Gy, 500-1000 Gy.

(ii) gamma irradiation at an irradiation dose of 10-2000 Gy. Examples include but are not limited to, 100-2000 Gy, 100-1500 Gy, 20-1500 Gy, 20-1000 Gy, 20-900 Gy, 20-800 Gy, 20-700 Gy, 20-600 Gy, 20-500 Gy, 20-400 Gy, 20-300 Gy, 20-200 Gy, 20-100 Gy, 100-1600 Gy, 100-1500 Gy, 100-1400 Gy, 100-1300 Gy, 100-800 1200, 100-1000 Gy, 100-900 Gy, 100-800 Gy, 100-700 Gy, 100-600 Gy, 100-500 Gy, 100-400 Gy, 100-300 Gy, 100-200 Gy, 200-2000 Gy, 200-1800 Gy, 200-1600 Gy, 200-1200 Gy, 200-1000 Gy, 200-800 Gy, 200-600 Gy, 200-400 Gy, 300-800 Gy, 300-700 Gy, 300-500 Gy, 50-600 Gy, 50-500 Gy, 50-400 Gy, 50-300 Gy, 50-200 Gy, 500-800 Gy, 500-1000 Gy.

(iii) Particle irradiation such as alpha, beta or other accelerated particle at an irradiation dose of 20-5000 Gy produced from a particle accelerator such as a linear accelerator;

Examples include but are not limited to, 20-5000 Gy, 100-5000 Gy, 100-4000 Gy, 100-3000 Gy, 100-2000 Gy, 100-1500 Gy, 20-1500 Gy, 20-1000 Gy, 20-900 Gy, 20-800 Gy, 20-700 Gy, 20-600 Gy, 20-500 Gy, 20-400 Gy, 20-300 Gy, 20-200 Gy, 20-100 Gy, 50-5000 Gy, 50-3000 Gy, 50-2000 Gy, 50-1000 Gy, 50-900 Gy, 50-800 Gy, 50-700 Gy, 50-600 Gy, 50-500 Gy, 50-400 Gy, 50-300 Gy, 50-200 Gy, 50-100 Gy, 100-1600 Gy, 100-1500 Gy, 100-1400 Gy, 100-1300 Gy, 100-800 1200, 100-1000 Gy, 100-900 Gy, 100-800 Gy, 100-700 Gy, 100-600 Gy, 100-500 Gy, 100-400 Gy, 100-300 Gy, 100-200 Gy, 300-800 Gy, 300-700 Gy, 300-500 Gy, 50-600 Gy, 50-500 Gy, 50-400 Gy, 50-300 Gy, 50-200 Gy, 500-800 Gy, 500-1000 Gy;

According to a specific embodiment the irradiation dose is 20-5000 Gy.

(iiii) UV-C radiation at an irradiation dose of 100 $\mu J/cm^2$-50 $J/cm^2$.

Examples include, but are not limited to, 100 $\mu J/cm^2$-50 $J/cm^2$, 1 $mJ/cm^2$-10 $J/cm^2$, 200 $\mu J/cm^2$-10 $J/cm^2$, 500 $\mu J/cm^2$-10 $J/cm^2$, 1 $mJ/cm^2$-10 $J/cm^2$, 15 $mJ/cm^2$-10 $J/cm^2$, 10 $mJ/cm^2$-10 $J/cm^2$, 20 $mJ/cm^2$-10 $J/cm^2$, 50 $mJ/cm^2$-10 $J/cm^2$, 100 $mJ/cm^2$-10 $J/cm^2$, 200 $mJ/cm^2$-10 $J/cm^2$, 300 $mJ/cm^2$-10 $J/cm^2$, 400 $mJ/cm^2$-10 $J/cm^2$, 500 $mJ/cm^2$-10 $J/cm^2$, 600 $mJ/cm^2$-10 $J/cm^2$, 700 $mJ/cm^2$-10 $J/cm^2$, 800 $mJ/cm^2$-10 $J/cm^2$, 900 $mJ/cm^2$-10 $J/cm^2$, 1 $J/cm^2$-10 $J/cm^2$, 2 $J/cm^2$-10 $J/cm^2$, 5 $J/cm^2$-10 $J/cm^2$.

It will be appreciated by the skilled artisan that the irradiation duration depends on the dose rate that the machine delivers to the treated sample. This parameter is dependent on various variables such as beam energy, distance between beam source and sample and filter that is used and are well known the artisan in the relevant field. For example, X-ray machine X-rad 320 without any filtration with source to sample distance (SSD) of 50 cm at 320 kV will deliver to the sample ~15 Gy/min, with filtration of 2 mm Aluminum or 1 mm Copper will deliver to the sample 3 Gy/min and with filter of 4 mm Copper will deliver 1 Gy/min. It is possible to increase the dose absorbed by the sample by decreasing the SSD thus, by changing SSD from 50 cm to 30 cm with filter of ~1 mmCu the sample will absorb ~8 Gy/min (instead of 3 Gy/min).

It is also possible to change the beam energy, for example, X-rad 160 machine will deliver to the sample more than 60 Gy/min at energy of 160 kV, 19 mA at SSD of 30 cm without any filtration and more than 6.5 Gy/min with filter of 2 mm Aluminum.

As duration depends on the dose rate, a dose of 20-1600 Gy can be achieved by 1 Gy/min up to 60 Gy/min. Therefore, it can range from 20 seconds to hours. According to a specific embodiment, X-rad 320 is used with 3 Gy/min (320 kV, 50 cm SSD, filter=2 mm Al). Accordingly radiation time can range from ~7 minutes to 9 hours.

According to a specific embodiment the radiation is gamma radiation for which various machines can be employed based on e.g., Cesium-137, Cobalt-60 or Iridium-192. The dose rate can vary from 1-300 Gy/min. According to a specific embodiment a BIOBEAM GM 8000 device is used with Cs137 that generates 2.8 Gy/min. Therefore, irradiation duration can vary from 7 minutes (=20 Gy) to ~12 hours (2000 Gy).

Following are non-limiting examples of commercial means for executing embodiments of the invention, though custom-made machines are also contemplated herein.

X-Ray Machines:
Vendor: Precision X-Ray

TABLE A

| Machine type: X-RAD | Output Voltage | SSD (Source to sample distance) | Filter type + width | i.e Gy/min |
|---|---|---|---|---|
| X-RAD 160 series | 5 KV-160 KV in 0.1 KV increments | 10 to 100 cm | No filter 2 mm Al | >60 Gy/min at 160 KV, 19 mA, 30 cm SSD >6.5 Gy/min at 160 KV, 19 mA, 30 cm SSD, (Filter = 2 mm Al) |

TABLE A-continued

| Machine type: X-RAD | Output Voltage | | SSD (Source to sample distance) | Filter type + width | i.e Gy/min |
|---|---|---|---|---|---|
| X-RAD 225 series | | | | | |
| X-RAD iR225 | 7.5 KV-225 KV in 0.1 KV increments | 0.1 mA to 45 mA in 0.01 mA increments | 10 to 95 cm | No filter 2 mm Al | 12 Gy/min at 225 KV, 13.3 mA, 30 cm SSD 6.4 Gy/min at 225 KV, 19 mA, 30 cm SSD, (Filter = 2 mm Al) |
| X-RAD 225 | 5 KV-225 KV in 0.1 KV increments | 0.1 mA to 45 mA in 0.01 mA increments | 15 cm to 63 cm | No filter 2 mm Al | Raw Beam: >60 Gy/min at 225 KV, 19 mA, 30 cm SSD Filtered Beam: >7.5 Gy/min at 225 KV, 19 mA, 30 cm SSD, (Filter = 2 mm Al) |
| X-RAD 225HP | 5-225 KV | 0.5 mA to 45 mA in 0.01 mA increments | 15 cm to 63 cm | No filter 2 mm Al | |
| X-RAD 225XL | 5-225 kV in 0.1 kV increments | 0.5 mA to 30 mA in 0.01 mA increments | 15 cm to 100 cm | No filter 2 mm Al | |
| X-RAD 320 series | | | | | |
| X-RAD 320 | 5 KV-320 KV in 0.1 KV increments | 0.5 mA to 45 mA in 0.01 mA increments | 20 cm to 90 cm | No filter 1 mm Cu 4 mm Cu | 3 Gy/min at 320 KV, 12.5 mA, 50 cm SSD, (HVL≈1 mm Cu) >15 Gy/min at 320 KV, 12.5 mA, 50 cm SSD |
| X-RAD 320Dx | 5 KV-320 KV in 0.1 KV increments | 0.5 mA to 45 mA in 0.01 mA increments | 20 cm to 90 cm | No filter 1 mm Cu 4 mm Cu | Same as above |
| X-RAD 320ix | 5 KV-320 KV in 0.1 KV increments | 0.5 mA to 45 mA in 0.01 mA increments | 20 cm to 90 cm | No filter 1 mm Cu 4 mm Cu | Same as above |
| X-RAD 350 series | 5-350 kV in 0.1 kV increments | 0.5 mA to 45 mA in 0.01 mA increments | | No filter 1.2 mm Cu 4 mm Cu | 3 Gy/min at 350 kV, 11.4 mA, 50 cm SSD, (HVL = 1.2 mm Cu) >1 Gy/min at 350 kV, 11.4 mA, 50 cm SSD, (HVL = 4.0 mm Cu) >15 Gy/min at 350 kV, 11.4 mA, 50 cm SSD, (unfiltered) |

TABLE A-continued

| Machine type: X-RAD | Output Voltage | SSD (Source to sample distance) | Filter type + width | i.e Gy/min |
|---|---|---|---|---|
| X-RAD 400/450 series | 5 KV-450 KV in 0.1 KV increments | 0.5 mA to 45 mA in 0.01 mA increments | 20 cm to 100 cm | 4 mm Cu | >4 Gy/min at 50 cm SSD (HVL = 4 mm Cu) |

*Al = Aluminum,
Cu = Copper

Other machines are available from RAD Source: www(dot)radsource(dot)com. Examples include, but are not limited to:
RS 3400
1. ~25 Gy Central Dose
2. 15 Gy/min/25 Gy central/50 Gy max
4 pi emitter
RS 2000
Available in 160 kV and 225 kV (Custom Built X-ray Irradiators with 350 kV are available).
Excellent for small animals irradiation with as doses rates ~1.2 Gy/min (120 rads/min)
3 mm cooper filter.
160 kv AT 225 kV
Other dose rates: for cells: >5 Gy/min (500 rads/min) filtered and up to 17 Gy/min unfiltered
RS 1800
Operates at 160 kV and 12.5 mA (2,000 watts)
RS 5000
utilizes MULTIPLE 4 pi emitters to achieve dose rates up to 120 Gy/min to a 500 mL canister
RS1300
4 pi X-ray Emitter (also described in U.S. Pat. No. 7,346,147)
~70 Gy/min for product density of 1.0 g/ml (3" diameter canister)
RS 2400 Featuring the 4 pi X-Ray Tube
Single 4 pi Au target X-ray Tube
Dose Rate: 420,000 rad/h (4.2 kGy/h) based on product density
RS 420
Faxitron www(dot)faxitron(dot)com/www(dot)faxitron(dot)com/application/biological-irradiation/
Tables B-H provide the specification for some commercially available irradiation devices that can be used in implementing the teachings of some embodiments of the invention.

TABLE B

| Specifications | MultiRad 160 | MultiRad 225 | MultiRad 350 |
|---|---|---|---|
| Energy range | Up to 160 kV | Up to 225 kV | Up to 350 kV |
| Tube current at max voltage | 25 mA | 17.8 mA | 11.4 mA |
| System power | 4000 W | 4000 W | 4000 W |
| Dose rate at max kVp & mA | Up to: 300 Gy/min (unfiltered) Up to: 32 Gy/min (2 mm Al) Up to: 16 Gy/min (0.3 mm Cu) | Up to: 285 Gy/min (unfiltered) Up to: 42 Gy/min (2 mm Al) Up to: 25 Gy/min (0.3 mm Cu) | Up to: 140 Gy/min (unfiltered) Up to: 40 Gy/min (2 mm Cu Al) Up to: 16.5 Gy/min (4.0 mm Cu HVL) |
| Focal spot size | 5.5 mm 1.2 mm for imaging (<0.5 IEC) | 5.5 mm 1.2 mm for imaging (<0.5 IEC) | 8 mm |
| Inherent filtration | 0.8 mm Be | 1.2 mm Be | 3 mm Be |
| Bean angle | 40° divergence | 40° divergence | 40° divergence |
| Bean coverage | 9 cm-40 cm diameter | 9 cm-40 cm diameter | 9 cm-40 cm diameter |
| Source to sample distance | 13 cm-65 cm | 13 cm-65 cm | 13 cm-65 cm |
| Exposure time | Programmable or continuous | Programmable or continuous | Programmable or continuous |
| Power requirements | 220 VAC +/− 10%, 50/60 Hz, single phase, 7.5 kVA | 220 VAC +/− 10%, 50/60 Hz, single phase, 7.5 kVA | 220 VAC +/− 10%, 50/60 Hz, single phase, 7.5 kVA |
| Cooling | Integrated closed-loop heat exchanger | Integrated closed-loop heat exchanger | Integrated closed-loop heat exchanger |
| Specimen turntable | Electrically-operated, 2 RPM, with integrated dosimeter | Electrically-operated, 2 RPM, with integrated dosimeter | Electrically-operated, 2 RPM, with integrated dosimeter |
| External dimensions | 74" H × 43" W × 35" D (188 cm × 108 cm × 88 cm) | 74" H × 43" W × 35" D (188 cm × 108 cm × 88 cm) | 74" H × 43" W × 35" D (188 cm × 108 cm × 88 cm) |
| Chamber dimensions | 23" H × 16" W × 17" D (58 cm × 41 cm × 43 cm) | 23" H × 16" W × 17" D (58 cm × 41 cm × 43 cm) | 23" H × 16" W × 17" D (58 cm × 41 cm × 43 cm) |
| Weight | 2120 lbs (960 kg) | 2550 lbs (1160 kg) | 3470 lbs (1575 kg) |

TABLE C

| Specifications | |
|---|---|
| Energy range | 10-130 kV |
| Tube current | 0.1-5 mA |
| Tube power | 650 W |
| Dose rate (130 kVp, 5.0 mA) | Up to > 45 Gy/min (unfiltered) Up to > 8 Gy/min (0.5 mm Al) |
| Focal spot size | 1.0 × 1.4 mm |
| Inherent filtration | 1.6 mm Be |
| Bean angle | 40° divergence |
| Bean coverage | 9 cm-27 cm diameter |
| Source to sample distance | 13 cm-38 cm |
| Exposure time | 5 sec to 180 min (1 sec increments) |
| Power requirements | 100-230 VAC +/− 10%, 50-60 Hz |
| cooling | Integrated closed-loop heat exchanger |
| Specimen turntable | Electrically operated, 2 RPM with integrated dosimeter |
| External dimensions | 30" H × 21" W × 24" D (77 cm × 53 cm × 61 cm) |
| Chamber dimensions | 14" H × 12" W × 12" D (37 cm × 30 cm × 32 cm) |
| weight | 460 lbs (210 kg) |
| Shipping weight | 540 lbs (245 kg) |

TABLE D

Faxitron cabinet X-ray System Model 43855C

SPECIFICATIONS
X-ray sources:

There are five X-ray sources offered with the Faxitron Model 43855C.
The system comes standard with a 110 kVp maximum source.
Standard source Energy Range-10-110 kVp
Tube Current-3.0 mA fixed*
Focal Spot-0.5 mm, nominal
X-Ray Tube-Stationary anode, glass tube with beryllium window (0.76 mm thick)
Beam Angle-30° divergence
Option A04

Energy Range-10-130 kVp
Tube Current-3.0 mA fixed*
Focal Spot-0.5 mm, nominal
X-Ray Tube-Stationary anode, glass tube with beryllium window (0.76 mm thick)
Beam Angle-30° divergence
Option A05

Energy Range-10-150 kVp
Tube Current-3.0 mA fixed*
Focal Spot-1.5 mm, nominal
X-Ray Tube-Stationary anode, glass tube with beryllium window (0.76 mm thick)
Beam Angle-40° divergence
Option M110

Energy Range-10-110 kVp
Tube Current-300 μA fixed*
Focal Spot-50 μm
-X-Ray Tube-Stationary anode, glass tube with beryllium window (0.76 mm thick)
Beam Angle-30° divergence
Option M130

Energy Range-10-130 kVp
Tube Current-300 μA fixed*
Focal Spot-50 μm
X-Ray Tube-Stationary anode, glass tube with beryllium window (0.76 mm thick)
Beam Angle-30° divergence X-ray generators are also available from Kimtron www(dot)kimtron(dot)com/products/

TABLE E

Polaris Generator Specifications

| Parameters | 160 kV | 225 kV Output | 320 kV | 450 kV |
|---|---|---|---|---|
| DC Output Voltage | 0-160 kV | 0-225 kV | 0 +−160 kV | 0 +− 225 kV |
| Max Output Current | 30 mA | 30 mA | 30 mA | 30 mA |
| Max Output Power | 3 kW | 3 kW | 4.2 kW | 4.2 kW |
| Polarity | Negative | Negative | Bi-Polar | Bi-Polar |

*All high voltage connectors are tapered with flanged fittings 160, 320, 450 or 600 kv Other X-ray generators are available from Xstrahl. For example, XenX:
Treatment distances: 30-38 cm or 80 cm FSD
Maximum Field Size: 18 cm circle at 35 cm FSD
Tube Voltage: 20-220 kV
Tube Current: 0-25 mA
XSTRAHL CABINET IRRADIATORS: CIX2, CIX3, CIXD
RS225 (Voltage Up to 220 kV Current 1.0 mA to 30 mA) and RS320 (Voltage Up to 300 kV Current Up to 30 mA) CIXD
Tube Voltage: 20-220 kV
Tube Current: 0-25 mA
Gamma Radiation Machines:
Examples of Gamma radiation machines include, but are not limited to:
BIOBEAM GM 2000/3000/8000-Radionuclide source: Cs-(137).

TABLE F

| | BIOBEAM GM 2000 | BIOBEAM GM 3000 | BIOBEAM GM 8000 |
|---|---|---|---|
| Dose rate | 2.5 Gy/min | 5 Gy/min | 5-2.6 Gy/min |

TABLE G

Gammacell ® 1000 Elite/3000 Elan-Radionuclide source: Cs-(137).

| | Gammacell ® 1000 Elite | Gammacell 3000 Elan |
|---|---|---|
| Dose rate | 3.5, 7.6 or 14.3 Gy/min | 4.5 or 8.7 Gy/min |

Gammabeam™ X200 (GBX200)-Cobalt-60 capacity of 434 TBq (11,725 Ci) that can deliver a dose rate of 800 cGy/min at 50 centimeters from the source at maximum field size.
A list of Radionuclide sources for gamma radiation appears in Table H below.

TABLE H

Data from U.S. NRC show that out of the thousands of manufactured and natural radionuclides, americium-241, cesium-137, cobalt-60, and iridium-192 account for nearly all (over 99 percent) of the Category 1 and 2 sources. The features of these and some other key radionuclide radiation sources are summarized in table S-1.
TABLE S-1 Summary of Radionuclides in Category 1 and 2 Radiation Sources in the United States[a]

| Radionuclide | Half-life | Radioactive Emissions and Energies | Typical Specific Activity (TBq/g) [Ci/g] | Total Activity in U.S. Inventory (TBq) [Ci] | Major Applications | Typical Activity (TBq) [Ci] | Physical or Chemical Form |
|---|---|---|---|---|---|---|---|
| Americium-241 | 432.2 y | α-5.64 MeV γ-60 keV, principal | 0.13 [3.5] | 240 [6,482] | Well logging | 0.5-0.8 [13-22] | Pressed powder (americium oxide) |
| Californium-252 | 2.645 y | α-6.22 MeV, Fission fragments, neutrons, and gammas | 20 [540] | 0.26 [7] | Well logging | 0.0004 [0.011] | Metal oxide |
| Cesium-137 (Ba-137m) | 30.17 y | β-518 keV max with γ-662 keV (94.4% of decays or β-1.18 MeV max | 0.75 [20] | 104,100 [2.8 million] | Self-contained irradiators Teletherapy Calibrators | 75 [2000] 50 [1400] 15 [400] | Pressed powder (cesium chloride) |
| Cobalt-60 | 5.27 y | γ-1.173 and 1.333 MeV | 3.7 [100] 11 [300] | 7.32 million [198 million] | Panoramic irradiators Self-contained irradiators Teletherapy industrial radiography | 150,000 [4 million] 900 [24,000] 500 [14,000] 4 [100] | Metal slugs Metal pellets |
| Iridium-192 | 74 d | β-1.46 MeV max with 2.3 γ-380 keV average, 1.378 MeV max (0.04% of decays) | 18.5 [500] | 5,436 [146,922] | Industrial radiography | 4 [100] | Metal |
| Plutonium-238 | 87.7 y | α-5.59 MeV, and γ-43 keV (30% of decays) | 2.6 [70] | 34.7 [937] | RTG Pacemakers (obsolete) Fixed gauges | 10 [270] 0.1 [3] 0.75 [20] | Metal oxide |

TABLE H-continued

Data from U.S. NRC show that out of the thousands of manufactured and natural radionuclides, americium-241, cesium-137, cobalt-60, and iridium-192 account for nearly all (over 99 percent) of the Category 1 and 2 sources. The features of these and some other key radionuclide radiation sources are summarized in table S-1.

TABLE S-1 Summary of Radionuclides in Category 1 and 2 Radiation Sources in the United States[a]

| Radionuclide | Half-life | Radioactive Emissions and Energies | Typical Specific Activity (TBq/g) [Ci/g] | Total Activity in U.S. Inventory (TBq) [Ci] | Major Applications | Typical Activity (TBq) [Ci] | Physical or Chemical Form |
|---|---|---|---|---|---|---|---|
| Selenium-75 | 119.8 d | γ-280 keV average, 800 keV max | 20-45 [530-1200] | 9.7 [261] | Industrial radiography | 3 [75] | Elemental or metal compound |
| Strontium-90 (Yttrium-90) | 28.9 y | β-546 keV | 5.2 [140] | 64,000 [1.73 million] | RTG | 750 [20,000] | Metal oxide |

[a]Nuclear decay data for this table and throughout the report are from Firestone and Shirly (1996).

Uv Machines:

Examples of UV radiation machines include, but are not limited to:

UV CROSS-LINKER CL-508 UVITEC Cambridge
UV Energy exposure: Min.0.025 Joules/Max. 99.99 Joules
UV exposure Time: Min.10 Seconds/Max.599 Minutes
Fisher Scientific™ UV Crosslinker AH
UVP CL-1000 and CX-2000 Crosslinkers: Maximum UV energy setting of 999,900 microjoules/cm2
Spectroline™ Microprocessor-Controlled UV Crosslinkers: 100 J/cm$^2$ to 0.9999 J/cm$^2$
BIO-LINK BLX: Energy-0-99.99 Joules/cm$^2$ Exposure Time: Up to 999.9 minutes Linear Accelerators:

Examples of linear accelerators that can be used in accordance with some embodiment s of the invention include, but are not limited to:

Basic Varian 600CD/6EX
Basic Varian 21/23 Series
Elekta Precise Systems
Elekta Synergy Platforms
Siemens Primus
Siemens Oncor
TomoTherapy Machines
Varian Trilogy
Varian iX
Elekta Synergy
Elekta Infinity
Cyberknife G4 & VSI
Elekta Versa HD
CyberKnife VSI
Varian TrueBeam.
Varian 21/23 series with OBI and RapidArc
Varian Trilogy with RapidArc
Cyberknife M6

As mentioned the pollen may be a harvested pollen (harvested prior to treating with the irradiation).

Alternatively, the pollen is a non-harvested pollen (e.g., on a whole plant). In such an embodiment, the pollen is harvested following treating.

There are various methods to achieve ionizing radiation. Sources of radiation include radioactive isotypes, particle accelerators and X-ray tubes.

Standard X-ray machines include superficial x-ray machines and orthovoltage X-ray machines. Examples include but are not limited to X-rad 160/225/320/350/400/450 series that the dose rate that they deliver can vary greatly and can range between 1-60 Gy/min, MultiRad 160/225/350 that can range between 16-300 Gy/min, CellRad that can range between 8-45 Gy/min or RAD source machines (examples include but are not limited to RS420/RS1300/RS1800/RS2000/RS2400/RS3400).

Gamma machines include various radioactive sources that can be Caesium-137, Cobalt-60 or Iridium-192. Examples of Caesium-137 Gamma radiation devices include, but are not limited to, BIOBEAM GM 2000/3000/8000 that generates between 2.5-5 Gy/min or Gammacell 1000 Elite/3000 Elan that generate between 3.5-14 Gy/min. Additional irradiators are particle accelerators such as Electrostatic particle accelerators and Electrodynamic (electromagnetic) particle accelerators such as Magnetic Induction Accelerators (such as Linear Induction Accelerators or Betatrons), Linear accelerators, Circular or cyclic RF accelerators (such as Cyclotrons, Synchrocyclotrons and isochronous cyclotrons Synchrotrons, Electron synchrotrons, Storage rings, Synchrotron radiation sources or FFAG accelerators).

An example of a cyclic accelerator is the linac. Other examples include, but are not limited to, microtrons, betatrons and cyclotrons. More exotic particles, such as protons, neutrons, heavy ions and negative π mesons, all produced by special accelerators, may be also used. Various types of linac accelerators are available: some provide X rays only in the low megavoltage range (4 or 6 MV), while others provide both X rays and electrons at various megavoltage energies. A typical modern high-energy linac will provide two photon energies (6 and 18 MV) and several electron energies (e.g. 6, 9, 12, 16 and 22 MeV) (Radiation Oncology Physics: A Handbook for Teachers and Students E. B. PODGORSAK).

Typical UV irradiation can be achieved by UV crosslinkers. UVC irradiators include, but are not limited to, Mercury-based lamps that emit UV light at the 253.7 nm line, Ultraviolet Light Emitting Diodes (UV-C LED) lamps that emit UV light at selectable wavelengths between 255 and 280 nm, Pulsed-xenon lamps emit UV light across the entire UV spectrum with a peak emission near 230 nm.

According to a specific embodiment, when the irradiation is X-ray the dose is not 300 Gy.

According to a specific embodiment, when the irradiation is gamma irradiation the dose is not 100, 300 and 500 Gy.

Examples of such treatments are provided in Examples 29 to 39 of the Examples section which follows.

Embodiments of the invention also refer to harvested pollen obtainable according to the method as described herein.

It will be appreciated that pollen obtained according to embodiments of the invention facilitate in fertilizing plants such that the aborted seeds per plant are uniform as manifested by a statistically significant average reduced weight that has a statistically significant reduced standard deviation as compared to naturally occurring aborted seeds per plant.

According to another specific embodiment, the average seed weight following pollen treatment at first generation is at least about 1.2 fold lower (e.g., 1.2-20, 1.2-15, 1.2-10, 1.2-8, 1.5-20, 1.5-15, 1.5-10, 1.5-8, 2-20, 2-15, 2-10, 2-8 fold lower) than that of an average seed of a control plant of the same developmental stage and of the same species fertilized by control pollen (not treated).

Additionally, the pollen is produced from a plant having an imbalanced chromosome number (genetic load) with the weed species of interest.

Thus, for example, when the weed of interest is diploid, the plant producing the pollen is treated with an agent rendering it polyploid, typically tetraploids are selected, such that upon fertilization with the diploid female plant an aborted or developmentally arrested, not viable seed set are created. Alternatively, a genomically imbalanced plant is produced which rarely produces a seed set.

According to a specific embodiment, the weed (or a regenerating part thereof or the pollen) is subjected to a polyploidization protocol using a polyploidy inducing agent, that produces plants which are able to cross but result in reduced productiveness.

Thus, according to some embodiments of the invention, the polyploid weed has a higher chromosome number than the wild type weed species (e.g., at least one chromosome set or portions thereof) such as for example two folds greater amount of genetic material (i.e., chromosomes) as compared to the wild type weed. Induction of polyploidy is typically performed by subjecting a weed tissue (e.g., seed) to a G2/M cycle inhibitor.

Typically, the G2/M cycle inhibitor comprises a microtubule polymerization inhibitor.

Examples of microtubule cycle inhibitors include, but are not limited to oryzalin, colchicine, colcemid, trifluralin, benzimidazole carbamates (e.g. nocodazole, oncodazole, mebendazole, R 17934, MBC), o-isopropyl N-phenyl carbamate, chloroisopropyl N-phenyl carbamate, amiprophosmethyl, taxol, vinblastine, griseofulvin, caffeine, bis-ANS, maytansine, vinbalstine, vinblastine sulphate and podophyllotoxin.

According to a specific embodiment, the microtubule cycle inhibitor is colchicine.

Still alternatively or additionally, the weed may be selected producing pollen that reduces fitness of the weed species of interest by way of subjecting it to a mutagenizing agent and if needed further steps of breeding.

Thus, weed can be exposed to a mutagen or stress followed by selection for the desired phenotype (e.g., pollen sterility, herbicide susceptibility).

Examples of stress conditions which can be used according to some embodiments of the invention include, but are not limited to, X-ray radiation, gamma radiation, UV radiation or alkylating agents such as NEU, EMS, NMU and the like. The skilled artisan will know which agent to select.

According to a specific embodiment, the stress is selected from the group consisting of X-ray radiation, gamma radiation, UV radiation, particle radiation such as alpha radiation, beta radiation or other accelerated particle radiation. For example, pollen of the weed can be treated with the agent that reduces the fitness (e.g., radiation) following harvest.

A specific description of such treatments are provided in Examples 19, 24, 25 and 26 of the Examples section which follows and should be considered as part of the specification.

Guidelines for plant mutagenesis are provided in K Lindsey Plant Tissue Culture Manual—Supplement 7: Fundamentals and Applications, 1991, which is hereby incorporated in its entirety.

Other mutagenizing agents include, but are not limited to, alpha radiation, beta radiation, neutron rays, heating, nucleases, free radicals such as but not limited to hydrogen peroxide, cross linking agents, alkylating agents, BOAA, DES, DMS, EI, ENH, MNH, NMH Nitrous acid, bisulfate, base analogs, hydroxyl amine, 2-Naphthylamine or alfatoxins.

Alternatively or additionally, the pollen may be genetically modified pollen (e.g., transgenic pollen, DNA-editing).

Thus, according to some embodiments of the invention the pollen of the invention confers reduced fitness by way of partial genome incompatibility, parthenocarpy, stenospermocarpy, reduced shattering, inhibition of seed dormancy, cleistogamy, induced triploidy, conditional lethality, male sterility, female sterility, inducible promoters, complete sterility by nonflowering, reduced biotic/abiotic stress tolerance. The skilled artisan will know which method to select.

According to a further aspect of the invention there is provided a method of producing pollen, the method comprising:
  (a) growing weed producing pollen that reduces fitness of at least one weed species of interest; and
  (b) harvesting said pollen.

Thus the pollen product producing weed is grown in dedicated settings, e.g., open or closed settings, e.g., a greenhouse. According to a specific embodiment, the growth environment for the manufacture of the pollen does not include crop plants or the weed species of interest. For example, the growth area includes a herbicide susceptible weed variant but not a herbicide resistant weed variant (of the same species). Another example, the growth environment comprises a GM weed with a destructor gene said weed being fertile and producing pollen, but doesn't include the weed in which the destructor gene is expressed.

According to a specific embodiment, growing said weed producing pollen that reduces fitness is effected in a large scale setting (e.g., hundreds to thousands $m^2$).

According to some embodiments of the invention, the weed producing pollen comprises only male plants.

According to some embodiments of the invention, the weed producing pollen comprises only male plants.

Harvesting pollen is well known in the art. For example, by the use of paper bags (Example 1). Another example is taught in U.S. 20060053686, which is hereby incorporated by reference in its entirety.

Once pollen is obtained it can be stored for future use. Examples of storage conditions include, but are not; limited to, storage temperatures in Celsius degrees e.g., −196, −160, −130, −80, −20, −5, 0, 4, 20, 25, 30 or 35; percent of relative humidity e.g., 0, 10, 20, 30, 40, 50, 60, 70, 80, 90 or 100. Additionally, the pollen can be stored in light or dark.

Alternatively, the pollen product of the present teachings is subjected to a post harvest treatment.

Thus, according to an aspect of the invention there is provided a method of producing pollen for use in artificial pollination, the method comprising:
  (a) obtaining pollen that reduces fitness of at least one weed species of interest, e.g., as described herein; and
  (b) treating said pollen for use in artificial pollination.

Accordingly, there is provided a composition of matter comprising weed pollen that reduces fitness of at least one weed species of interest, said pollen having been treated for improving its use in artificial pollination.

Examples of such treatments include, but are not limited to coating, priming, formulating, chemical inducers, physical inducers [e.g., potential inducers include, but are not limited to, ethanol, hormones, steroids, (e.g., dexamethasone, glucocorticoid, estrogen, estradiol), salicylic acid, pesticides and metals such as copper, antibiotics such as but not limited to tetracycline, Ecdysone, ACEI, Benzothiadiazole and Safener, Tebufenozide or Methoxyfenozide], solvent solubilization, drying, heating, cooling and irradiating (e.g., gamma, UV, X-ray).

According to a specific embodiment, the pollen is resistant to a herbicide. In such a case the pollen may be coated with the herbicide so as to reduce competition with native pollen that is sensitive to the herbicide.

Additional ingredients and additives can be advantageously added to the pollen composition of the present invention and may further contain sugar, potassium, calcium, boron, and nitrates. These additives may promote pollen tube growth after pollen distribution on flowering plants.

In some embodiments, the pollen composition of the present invention contains dehydrated or partially dehydrated pollen.

Thus, the pollen composition may comprise a surfactant, a stabilizer, a buffer, a preservative, an antioxidant, an extender, a solvent, an emulsifier, an invert emulsifier, a spreader, a sticker, a penetrant, a foaming agent, an anti-foaming agent, a thickener, a safener, a compatibility agent, a crop oil concentrate, a viscosity regulator, a binder, a tacker, a drift control agent, a fertilizer, a timed-release coating, a water-resistant coating, an antibiotic, a fungicide, a nematicide, a herbicide or a pesticide.

Other ingredients and further description of the above ingredients is provided hereinbelow.

Under ordinary conditions of storage and use, the composition of the present invention may contain a preservative to prevent the growth of microorganisms.

The preventions of the action of microorganisms can be brought about by various antibacterial and antifungal agents, for example, parabens, chlorobutanol, sorbic acid, and the like. Antioxidants may also be added to the pollen suspension to preserve the pollen from oxidative damage during storage. Suitable antioxidants include, for example, ascorbic acid, tocopherol, sulfites, metabisulfites such as potassium metabisulfite, butylhydroxytoluene, and butylhydroxyanisole.

Thus, pollen compositions that may also be used but not limited to mixtures with various agricultural chemicals and/or herbicides, insecticides, miticides and fungicides, pesticidal and biopesticidal agents, nematocides, bactericides, acaricides, growth regulators, chemosterilants, semiochemicals, repellents, attractants, pheromones, feeding stimulants or other biologically active compounds all of which can be added to the pollen to form a multi-component composition giving an even broader spectrum of agricultural protection.

Thus in the artificial pollination method of the present invention can be applied together with the following herbicides but not limited to: ALS inhibitor herbicide, auxin-like herbicides, glyphosate, glufosinate, sulfonylureas, imidazolinones, bromoxynil, delapon, dicamba, cyclohezanedione, protoporphyrionogen oxidase inhibitors, 4-hydroxyphenyl-pyruvate-dioxygenase inhibitors herbicides.

In some embodiments, the pollen can be combined with appropriate solvents or surfactants to form a formulation. Formulations enable the uniform distribution of a relatively small amount of the pollen over a comparatively large growth area. In addition to providing the user with a form of a pollen that is easy to handle, formulating can enhance its fertilization activity, improve its ability to be applied to a plant, enable the combination of aqueous-soluble and organic-soluble compounds, improve its shelf-life, and protect it from adverse environmental conditions while in storage or transit.

Numerous formulations are known in the art and include, but are not limited to, solutions, soluble powders, emulsifiable concentrates, wettable powders, liquid flowables, and dry flowables. Formulations vary according to the solubility of the active or additional formulation ingredients in water, oil and organic solvents, and the manner the formulation is applied (i.e., dispersed in a carrier, such as water, or applied as a dry formulation).

Solution formulations are designed for those active ingredients that dissolve readily in water or other non-organic solvents such as methanol. The formulation is a liquid and comprises of the active ingredient and additives.

Suitable liquid carriers, such as solvents, may be organic or inorganic. Water is one example of an inorganic liquid carrier. Organic liquid carriers include vegetable oils and epoxidized vegetable oils, such as rape seed oil, castor oil, coconut oil, soybean oil and epoxidized rape seed oil, epoxidized castor oil, epoxidized coconut oil, epoxidized soybean oil, and other essential oils. Other organic liquid carriers include aromatic hydrocarbons, and partially hydrogenated aromatic hydrocarbons, such as alkylbenzenes containing 8 to 12 carbon atoms, including xylene mixtures, alkylated naphthalenes, or tetrahydronaphthalene. Aliphatic or cycloaliphatic hydrocarbons, such as paraffins or cyclohexane, and alcohols, such as ethanol, propanol or butanol, also are suitable organic carriers. Gums, resins, and rosins used in forest products applications and naval stores (and their derivatives) also may be used. Additionally, glycols, including ethers and esters, such as propylene glycol, dipropylene glycol ether, diethylene glycol, 2-methoxyethanol, and 2-ethoxyethanol, and ketones, such as cyclohexanone, isophorone, and diacetone alcohol may be used. Strongly polar organic solvents include N-methylpyrrolid-2-one, dimethyl sulfoxide, and N,N-dimethylformamide.

Soluble powder formulations are similar to solutions in that, when mixed with water, they dissolve readily and form a true solution. Soluble powder formulations are dry and include the active ingredient and additives.

Emulsifiable concentrate formulations are liquids that contain the active ingredient, one or more solvents, and an emulsifier that allows mixing with a component in an organic liquid carrier. Formulations of this type are highly concentrated, relatively inexpensive per pound of active ingredient, and easy to handle, transport, and store. In addition, they require little agitation (will not settle out or separate) and are not abrasive to machinery or spraying equipment.

Wettable powders are dry, finely ground formulations in which the active ingredient is combined with a finely ground carrier (usually mineral clay), along with other ingredients to enhance the ability of the powder to suspend in water. Generally, the powder is mixed with water for application. Typical solid diluents are described in Watkins et al., Handbook of Insecticide Dust Diluents and Carriers, 2nd Ed., Dorland Books, Caldwell, N.J. The more absorptive diluents are preferred for wettable powders and the denser ones for dusts.

Liquid flowable formulations are made up of finely ground active ingredient suspended in a liquid. Dry flowable and water-dispersible granule formulations are much like wettable powders except that the active ingredient is formulated on a large particle (granule) instead of onto a ground powder.

The methods of making such formulations are well known. Solutions are prepared by simply mixing the ingredients. Fine, solid compositions are made by blending and, usually, grinding, as in a hammer or fluid energy mill. Suspensions are prepared by wet-milling (see, for example, U.S. Pat. No. 3,060,084).

The concentration of a pollen growth stimulating compound in a formulation may vary according to particular compositions and applications.

In some embodiments of the disclosure, inactive ingredients i.e., adjuvants) are added to pollen to improve the performance of the formulation. For example, in one embodiment of the disclosure, pollen is formulated with a surfactant. A surfactant (surface active agent) is a type of adjuvant formulated to improve the dispersing/emulsifying, absorbing, spreading, and sticking properties of a spray mixture. Surfactants can be divided into the following five groupings: (1) non-ionic surfactants, (2) crop oil concentrates, (3) nitrogen-surfactant blends, (4) esterified seed oils, and (5) organo-silicones.

Suitable surfactants may be nonionic, cationic, or anionic, depending on the nature of the compound used as an active ingredient. Surfactants may be mixed together in some embodiments of the disclosure. Nonionic surfactants include polyglycol ether derivatives of aliphatic or cycloaliphatic alcohols, saturated or unsaturated fatty acids and alkylphenols. Fatty acid esters of polyoxyethylene sorbitan, such as polyoxyethylene sorbitan trioleate, also are suitable nonionic surfactants. Other suitable nonionic surfactants include water-soluble polyadducts of polyethylene oxide with polypropylene glycol, ethylenediaminopolypropylene glycol and alkylpolypropylene glycol. Particular nonionic surfactants include nonylphenol polyethoxyethanols, polyethoxylated castor oil, polyadducts of polypropylene and polyethylene oxide, tributylphenol polyethoxylate, polyethylene glycol and octylphenol polyethoxylate. Cationic surfactants include quaternary ammonium salts carrying, as N-substituents, an 8 to 22 carbon straight or branched chain alkyl radical.

The quaternary ammonium salts carrying may include additional substituents, such as unsubstituted or halogenated lower alkyl, benzyl, or hydroxy-lower alkyl radicals. Some such salts exist in the form of halides, methyl sulfates, and ethyl sulfates. Particular salts include stearyldimethylammonium chloride and benzyl bis(2-chloroethyl)ethylammonium bromide.

Suitable anionic surfactants may be water-soluble soaps as well as water-soluble synthetic surface-active compounds. Suitable soaps include alkali metal salts, alkaline earth metal salts, and unsubstituted or substituted ammonium salts of higher fatty acids. Particular soaps include the sodium or potassium salts of oleic or stearic acid, or of natural fatty acid mixtures. Synthetic anionic surfactants include fatty sulfonates, fatty sulfates, sulfonated benzimidazole derivatives, and alkylarylsulfonates. Particular synthetic anionic surfactants include the sodium or calcium salt of ligninsulfonic acid, of dodecyl sulfate, or of a mixture of fatty alcohol sulfates obtained from natural fatty acids. Additional examples include alkylarylsulfonates, such as sodium or calcium salts of dodecylbenzenesulfonic acid, or dibutylnaphthalenesulfonic acid. Corresponding phosphates for such anionic surfactants are also suitable.

Other adjuvants include carriers and additives, for example, wetting agents, such as anionic, cationic, nonionic, and amphoteric surfactants, buffers, stabilizers, preservatives, antioxidants, extenders, solvents, emulsifiers, invert emulsifiers, spreaders, stickers, penetrants, foaming agents, anti-foaming agents, thickeners, safeners, compatibility agents, crop oil concentrates, viscosity regulators, binders, tackers, drift control agents, or other chemical agents, such as fertilizers, antibiotics, fungicides, nematicides, or pesticides (others are described hereinabove). Such carriers and additives may be used in solid, liquid, gas, or gel form, depending on the embodiment and its intended application.

As used herein "artificial pollination" is the application, by hand or dedicated machinery, of fertile stigmas with the pollen from plants with desired characteristics, as described herein.

Artificial pollination in the field can be achieved by pollen spraying, spreading, dispersing or any other method. The application itself will be performed by ground equipment, aircraft, unmanned aerial vehicles (UAV), remote-piloted vehicles(RPV), drones or specialized robots, special vehicles or tractors, animal assisted, specialized apparatus that is designed to spread boosts of pollen, specialized apparatus that combines ventilation and spraying of pollen to enhance recycling of pollen or any other application method or apparatus wherein application can be of a single dose, multiple doses, continuous, on an hourly/daily/weekly/monthly basis or any other application timing methodology.

Example 2 below (which is hereby incorporated into this section in its entirety) describes a number of embodiments for artificial pollination by hand, including:

(i) Direct application using paper bags;

(ii) Simple pollen dispersal above the female inflorescence (single application of total amount); or (iii) Continuous pollen spraying above the female inflorescence.

It will be appreciated that at any time the weed of interest can be further treated with other weed control means. For example, the weed may be treated with a herbicide (which is usually applied at early stages of germination as opposed to the pollen which is applied at flowering). Thus a herbicide for instance can be applied prior to, concomitantly with or following pollen treatment.

Any of the pollen compositions described herein can be produced as a single species pollen with a single trait for reducing weed fitness, a single species pollen with a plurality of traits for reducing weed fitness (e.g., a number of different herbicide resistances or a number of sterility encoding mechanisms) all introduced into a single weed or to a plurality of weeds of the same species, a multispecies pollen with a single trait or a multispecies pollen with a plurality of said traits.

Thus, commercial products can be manufactured as kits whereby each pollen type is packed in a separate packaging means (e.g., bag), or two or more types of pollen are combined into a single composition and packed in a single packaging means (e.g., bag). The product may be accompanied by instructions for use, regulatory information, product description and the like.

The kit may also include in a separate packaging means other active ingredients such as at least one of a chemical inducer (as described above), herbicide, fertilizer, antibiotics and the like.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Pollen Collection—Amaranthaceae, Poaceae, Asteraceae

Paper bags are used for pollen collection. Pollen is collected at morning (9:00 AM) by carefully inserting a male inflorescence into a paper bag and gently tapping the bag to release the pollen off the anthers. This collection process is repeated until pollen dust is visible inside the paper bags. Pollen grains are collected and pooled from multiple male plants. Each paper bag is weighed and the average pollen amount generated from a single male inflorescence and a single plant is calculated.

Example 2

Calibration of Pollen Amounts Needed for Optimal Pollination and Comparison Between Different Application Methods for Diecious Species—*Amaranthus palmeri*, *Amaranthus tuberculatus*

The experiment compares three pollen doses under four different application methods each group contains three female plants that are pollinated. In addition, one group of female plants is not pollinated at all and is used as control for apomixis levels. In all cases female plants are kept isolated from male plants. The doses that are used are approximately equivalent to pollen harvested from 0.1, 1, 10 total pollen of male plants, respectively. The application methods compared are: (i) Direct application using paper bags, (ii) Simple pollen dispersal above the female inflorescence (single application of total amount) (iii) Simple pollen dispersal above the female inflorescence (4 applications in intervals of 2 days, each application of 0.25 of the total amount of pollen dose) (iv) Continuous pollen spraying above the female inflorescence for 1 hour (the overall dose applied is identical to other treatments).

Pollen application by paper bags is conducted as follows: four paper bags with pollen and one paper bag without pollen are put on each of five flowering spikes randomly chosen. The spikes are longer than the paper bags, therefore, a label is attached just below the paper bag to mark the portion of the spike that is exposed to pollen. The paper bag with no pollen is used as a control.

Pollen application by simple pollen dispersal is conducted as follows: pollen is dispersed above the inflorescences of the female plants from 50 cm distance of the average female plant height. The pollen application process is repeated 4 times in application method iii.

Continuous pollen application by spraying is conducted from the same height as in application method ii for 1 hour.

14 days post pollination, seeds are harvested. In the paper bags method, the number of seeds per cm of spike is determined and in all other methods the number of seeds per female plant is determined.

TABLE 2

| Application method | Amount of pollen applied (as estimated from N male plants) | Single dose/ Multiple dose continuous application |
|---|---|---|
| Paper bags (i) | N = 0.1 | Single dose |
| Paper bags (i) | N = 1 | Single dose |
| Paper bags (i) | N = 10 | Single dose |
| Pollen dispersal (ii) | N = 0.1 | Single dose |
| Pollen dispersal (ii) | N = 1 | Single dose |
| Pollen dispersal (ii) | N = 10 | Single dose |
| Pollen dispersal (iii) | N = 0.1 | Multiple doses |
| Pollen dispersal (iii) | N = 1 | Multiple doses |
| Pollen dispersal (iii) | N = 10 | Multiple doses |
| Pollen spraying (iv) | N = 0.1 | Continuous |
| Pollen spraying (iv) | N = 1 | Continuous |
| Pollen spraying (iv) | N = 10 | Continuous |

Example 3

Calibration of Pollen Amounts Needed for Optimal Pollination and Comparison Between Different Application Methods for Monocious Species—*Lolium rigidum*, *Ambrosia trifida*, *Ambrosia artemisiifolia* and *Sorghum halepense*

This example is conducted similarly to Example 2 but rather instead of using female plants, all the male inflorescence on the pollinated plants are covered by paper bags in order to avoid self-pollination.

Example 4

Achieving Enhanced Susceptibility to Acetolactate Synthase (ALS) Inhibitors or EPSP Synthase Inhibitors by Pollen Application in Growth Rooms in *A. palmeri* and *A. tuberculatus*

*A. palmeri* resistant to ALS inhibitors seeds (Horak M J et al., 1997, Heap I, 2016) are germinated on soil and seedlings are transferred and transplanted into pots. When plants begin to flower, they are closely monitored daily to identify female plants at an early stage. Identified female plants are immediately transferred to another growth room to avoid being pollinated. Ten ALS resistant female plants are transferred into larger pots to allow full growth in size. 2 days after the transfer to large pots, female plants are divided into 2 groups of 5 female plants and each group is placed in a separate growth room having the same conditions and the plants continue to grow. At flowering time pollination procedure is conducted. In each separate room 5 female plants are pollinated by simple dispersal. In one room, the dispersed pollen was collected from males susceptible to ALS inhibitors (seeds obtained from Agriculture Research Service National Plant Germplasm System plant introduction as well as from various locations in Israel) and in the other room the dispersed pollen was collected from males resistant to ALS inhibitors. After 24 hours all the 10 female plants are transferred to the same room and seeds are harvested 14 days after the pollination event.

From each female plant, 100 seeds are taken and split into 2. Each set of 50 seeds are planted in trays of 15 by 15 cm. One tray is covered with a thin layer of soil before spraying the ALS inhibitor (ALS inhibitor—Atlantis, 2+10 g/L OD, Bayer is sprayed according to manufacturer instructions—25+120 g/ha). Control trays are not sprayed. Emerging seedlings are counted 14 days after spraying. Emergence in control trays is used to estimate the potential total number of germinating seeds in sprayed trays of the same seed source. The proportion of resistance to ALS inhibitors is compared between the two progeny populations. The reduction in this proportion between the groups pollinated with resistant pollen and susceptible one reflects the effect of the susceptibility property that can be inherited by crossing these two specific susceptible and resistant varieties.

TABLE 3

| Female plants | Pollen source | Resistance estimation in progeny (as calculated from the number of seedlings that emerge out of 50 following herbicide application) |
|---|---|---|
| 5 resistant plants $F_R$ | Pollen from resistant plants $M_R$ | $N^R(F_R \times M_R)$-Number of resistant seedlings |
| 5 resistant Plants $F_R$ | Pollen from susceptible plants $M_s$ | $N^R(F_R \times M_s)$-Number of resistant seedlings |

Susceptibility inheritance = $1 - N^R(F_R \times M_s)/N^R(F_R \times M_R)$

A similar experiment is conducted using seeds from *A. palmeri* resistant to EPSP synthase inhibitors seeds (Culpepper A S et al. 2006, Heap I, 2016) where EPSPS inhibitor is used for selection (EPSPS inhibitor—ROUNDUP, 360 g/l SL, MONSANTO is sprayed according to manufacturer instructions—720 g/ha).

Separately, the experiment is repeated in an identical setup using *A. tuberculatus* resistant to ALS inhibitor seeds (Patzoldt W L et al., 2002, Heap I, 2016) or *A. tuberculatus* resistant to EPSP synthase inhibitors seeds (Vijay K. et al. 2013, Heap I, 2016). The source of susceptible seeds is from Agriculture Research Service National Plant Germplasm System plant introduction as well as from various locations in Israel.

Example 5

Achieving Enhanced Susceptibility to ALS or EPSPS Inhibitors by Pollen Application Under Competitive Conditions in Growth Rooms in *A. palmeri* and *A. tuberculatus*

*Palmeri* plants resistant to ALS inhibitors or EPSPS inhibitors (seeds source same as in Example 4) are grown and the separation between female and male plants is conducted as described in Example 4. At flowering time, two plots are being established, each of size 4×4 m, each containing together 5 females and 4 males plants. Both plots contain only resistant plants (both female and males). The two plots are located in separate growth rooms in order to avoid pollen cross contamination.

Pollen harvested from susceptible male plants is being dispersed on one of the plots and plants continue to grow for 14 days and then harvested. From each female plant, 100 seeds are collected and split into 2 sets. Each set of 50 seeds is planted in trays of 15×15 cm. One tray is covered with a thin layer of soil before spraying the ALS inhibitor or EPSPS inhibitor.

Control trays are not sprayed. Emerging seedlings are counted 14 days after spraying. Emergence in control trays is used to estimate the potential total number of germinating seeds in sprayed trays of the same seed source.

The proportion of resistance to ALS inhibitors or EPSPS inhibitors is compared between the progeny population originated from the two plots with and without the additional susceptible pollen. The enhanced susceptibility to ALS inhibitors or EPSPS inhibitors between the plots with the artificial pollination relatively to the one without it shows the efficacy of the artificial pollination under competitive conditions.

Example 6

Achieving Enhanced *Lolium rigidum* Susceptibility to ALS/EPSPS Inhibitor by Pollen Application in Growth Rooms

*L. rigidum* resistant to ALS inhibitor or EPSPS inhibitor seeds (Matzrafi M and Baruch R, 2015) are germinated on soil and seedlings are transferred and transplanted into pots. The experiment is conducted as described in Example 4.

Example 7

Achieving Enhanced *Ambrosia artemisiifolia* (Common Ragweed) Susceptibility to ALS/EPSPS Inhibitor by Pollen Application Under Competitive Conditions in Growth Rooms

*A. artemisiifolia* resistant to EPSPS inhibitor seeds (Heap I, 2016) is germinated on soil and seedlings are transferred and transplanted into pots. Ten female plants are taken and divided into two groups of 5. Each group is placed in separate growth rooms with similar conditions to avoid cross-pollination. When plants begin to flower, one group is being artificially pollinated by dispersal of pollen harvested from male plants susceptible to EPSPS inhibitor while the other group is not artificially pollinated.

As the *Ambrosia* species is monoecious, the artificial pollination that is conducted here is under competitive conditions as native pollen exists at the flowering period. Seeds are harvested 14 days after the pollination event.

From each female plant, 100 seeds are collected and split into 2 sets. Each set of 50 seeds is planted in trays of 15×15 cm. One tray is covered with a thin layer of soil before spraying with ALS/EPSPS inhibitor. (ALS inhibitor—Atlantis, 2+10 g/L OD, Bayer is sprayed according to manufacturer instructions—25+120 g/ha, EPSPS inhibitor—ROUNDUP, 360 g/l SL, MONSANTO is sprayed according to manufacturer instructions—720 g/ha).

Control trays are not sprayed but are only covered with a thin layer of soil. Emerging seedlings are counted 14 days after spraying. Emergence in control trays is used to estimate the potential total number of germinating seeds in sprayed trays of the same seed source. The proportion of resistance to ALS/EPSPS inhibitor is compared between the two progeny populations. The reduction in this proportion between the groups pollinated with susceptible pollen and the one not artificially pollinated reflects the efficacy of the pollination treatment in monoecious species such as *ambrosia*.

TABLE 4

| Female plants | Pollen source | Resistance estimation in progeny (as calculated from the number of seedlings emerge out of 50 following herbicide application) |
|---|---|---|
| 5 resistant plants $F_R$ | 5 resistant plants $M_R$ | $N^R(F_R \times M_R)$-Number of resistant seedlings |
| 5 resistant Plants $F_R$ | 5 Resistant plants + pollen from susceptible plants $M_R + M_s$ | $N^R(F_R \times (M_R + M_s))$-Number of resistant seedlings |

Efficacy of the artificial pollination under competitive conditions = $1 - N^R(F_R \times (M_R + M_s))/ N^R(F_R \times M_R)$

TABLE 5

| # of plants | Pollen source (native/external) | Resistance estimation in progeny (as calculated from the number of seedlings emerge out of 50 following herbicide application) |
|---|---|---|
| 5 resistant plants (R) | Native pollen only (R) | $N^R$(R × R)-Number of resistant seedlings |
| 5 resistant Plants (R) | Native pollen (R) + external application (S) | $N^R$(R × (R + S))-Number of resistant seedlings |

Efficacy of treatment for susceptibility inheritance = $1 - N^R(R \times (R + S))/N^R(R \times R)$

Example 8

Achieving Enhanced *Ambrosia trifida* (Giant Ragweed) Susceptibility to ALS/EPSPS Inhibitor by Pollen Application Under Competitive Conditions in Growth Rooms Experiment is conducted and evaluated as described in Example 7 with *Ambrosia trifida* instead of *Ambrosia artemisiifolia.*

Example 9

Generation and Evaluation of a "Super Herbicide Sensitive" Weed by Breeding of *A. palmeri, A. tuberculatus*

To produce super herbicide sensitive pollen from *A. palmeri* the following selection for highest sensitivity to various herbicides was performed:

1. *A. palmeri* line with highest sensitivity to EPSP synthase inhibitors mode of action was first picked in the following way: application of EPSPS inhibitor at 0.125×, 0.25×, 0.5×, 1× and 2×, where x is the standard recommended levels of glyphosate. Clones of plants that died from 0.125× were allowed to produce seed and were further subjected to recurrent selection to generate the most sensitive plants (S lines), which died from 0.125× glyphosate.

2. *A. palmeri* with highest sensitivity to ALS inhibitors mode of action was picked by application of ALS inhibitor at 0.125×, 0.25×, 0.5×, 1× and 2×, where x is the standard recommended levels of ALS inhibitor. Clones of plants that died from 0.125× were allowed to produce seed and were further subjected to recurrent selection to generate the most sensitive plants (S lines), which died from 0.125×ALS inhibitor.

3. *A. palmeri* with highest sensitivity to Acetyl CoA Carboxylase (ACCase) inhibitors mode of action was picked by application of ACCase inhibitor at 0.125×, 0.25×, 0.5×, 1× and 2×, where x is the standard recommended levels of ACCase inhibitor. Clones of plants that died from 0.125× were allowed to produce seed and were further subjected to recurrent selection to generate the most sensitive plants (S lines), which died from 0.125× ACCase inhibitor.

The *A. palmeri* lines obtained by the methods described herein may be further crossed by traditional breeding techniques to obtain a plant weed line that is "Super herbicide sensitive" to multiple modes of actions.

Evaluation of enhanced *A. palmeri* susceptibility to EPSP synthase inhibitors, ALS inhibitors and Acetyl CoA Carboxylase (ACCase) inhibitors by pollen application in growth rooms is conducted as described in Example 4 with the usage of multiple herbicides instead of one herbicide.

The same procedure to obtain "super herbicide sensitive" is done with *A. tuberculatus.*

Example 10

Generation and Evaluation of the Sterility Property of *A. palmeri* or *A. tuberculatus* Transformed with "Terminator Technology" Genes As previously described in U.S. Pat. No. 5,925,808, 3 plasmids are being used for *A. palmeri* or *A. tubercultus* transformation.

1. a gene which expression results in an altered plant phenotype linked to a transiently active promoter, the gene and promoter being separated by a blocking sequence flanked on either side by specific excision sequences.

2. A second gene that encodes a recombinase specific for the specific excision sequences linked to a repressible promoter.

3. A third gene that encodes the repressor specific for the repressible promoter.

Plasmid sequences and procedures are used as described in U.S. Pat. No. 5,925,808, supra:

1. The death gene used is RIP (ribosomal inactivating protein, sequence of a complete RIP gene, saporin 6:GenBank ID SOSAP6, Accession No. X15655) or barnase (Genbank Accession M14442)

2. Construction of a CRE Gene under the control of a Tetracycline-derepressible 35S Promoter.

3. Third plasmid is Tet Repressor Gene Driven by a 35S Promoter.

The transiently active promoter in the first plasmid is replaced with *A. palmeri* promoter or *A. tuberculatus* that is expressed during embryogenesis, seed development or seed germination. *A. palmeri* or *A. tuberculatus* transformation is carried out as previously described in Pal A., et al 2013. A stably transformed line that highly expresses the desired plasmids is picked for further stages.

Seeds from this *A. palmeri* or *A. tuberculatus* line are split into two groups: one group is treated with tetracycline whereas the other group is left untreated. The plants are grown and identified males from each group are picked for the evaluation stage.

Evaluation of the efficiency of sterility in the transformed line is conducted in the following way: Two plots are being established at flowering time: 1. Containing 5 natural female *A. palmeri* or *A. tuberculatus* plants with 4 males from this transformed line that are not treated with tetracycline in the seed stage. 2. Containing 5 natural female *A. palmeri* or *A. tuberculatus* plants with 4 males from this genetically modified line that is treated with tetracycline in the seed stage. Plants continue to grow for 14 days and then seeds are being harvested. Two measures are being estimated: 1. Total count and weight of seeds produced from each female plant where the difference between the counts and weights between the two groups represent sterility efficiency. 2. From each female plant 50 seeds are taken and planted and the number of emerged seedlings is counted at the age of 14 days. The sterility efficiency is estimated from these two parameters.

TABLE 6

| Female plants | Pollen source | Seeds count and weight | Seedling emergence estimation in progeny (as calculated from the number of seedlings emerge out of 50) |
|---|---|---|---|
| 5 female plants F | 5 males with the "terminator technology" without tetracycline treatment $M_{T-tet}$ | $N_{seeds}(F \times M_{T-tet})$ – seed count $W_{seeds}(F \times M_{T-tet})$ – total seed weight | $N_{seedlings}(F \times M_{T-tet})$- Number of seedlings |
| 5 female plants F | 5 males with the "terminator technology" with tetracycline treatment $M_{T+tet}$ | $N_{seeds}(F \times M_{T+tet})$ – seed count $W_{seeds}(F \times M_{T+tet})$ – total seed weight | $N_{seedlings}(F \times M_{T+tet})$- Number of seedlings |

Efficacy of Sterility by number of seeds or seedlings = $1 - (N(F \times M_{T+tet})/N(F \times M_{T-tet}))$ An alternative set of plasmids that are used are based on the Tet ON system in which the rtTA (reverse tetracycline controlled transactivator) protein is capable of binding the operator only if bound by a tetracycline and as a consequence activates transcription:

1. a gene which expression results in an altered plant phenotype linked to a transiently active promoter, the gene and promoter being separated by a blocking sequence flanked on either side by specific excision sequences.

2. A second gene that encodes a recombinase specific for the specific excision sequences linked to an operator that is upstream to the promoter and is responsive to an activator.

3. A third gene that encodes the activator specific for the operator in the second plasmid. Under one instance the activator can be regulated by an inducible promoter. Alternatively, the inducer can bind the activator protein eliciting a conformational change to its active form.

Plasmid sequences are:

1. The death gene used is RIP (ribosomal inactivating protein, sequence of a complete RIP gene, saporin 6:GenBank ID SOSAP6, Accession No. X15655) or barnase (Genbank Accession M14442) under the control of a specific embryogenesis, seed development or germination promoter.

2. Construction of a CRE Gene under the control of a Tetracycline-responsive element (TRE).

3. Third plasmid is a 35S promoter upstream of a fusion of a Tet Repressor Gene, reverse TetR (reverse tetracycline repressor), found in *Escherichia coli* bacteria, with the activation domain of another protein, VP16, found in the Herpes Simplex Virus (termed rtTA).

Upon application of tetracycline or its derivatives such as doxycycline the rtTA becomes activated and results in expression of the CRE recombinase and consequently activation of the death gene.

Another set of plasmids that are used is based on only two sets of plasmids:

1. a gene which expression results in an altered plant phenotype linked to a transiently active promoter and an operator that is upstream to the promoter and is responsive to an activator.

2. A second gene that encodes the activator specific for the operator from the first plasmid which is activated upon induction. Plasmid sequences are:

1. The death gene used is RIP (ribosomal inactivating protein, sequence of a complete RIP gene, saporin 6:GenBank ID SOSAP6, Accession No. X15655) or barnase (Genbank Accession M14442) under the control of a specific embryogenesis, seed developmentor germination promoter and upstream to the promoter a TRE sequences.

2. A constitutive promoter upstream of a rtTA gene.

Upon application of tetracycline or its derivatives such as doxycycline the rtTA becomes activated and results in activation of the death gene.

Similar experimental setups are repeated with both plasmid sets explained above and the efficiency of sterility is calculated and evaluated as explained with the first plasmid set.

Example 11

Generation and Evaluation of the Sterility Property in *A. palmeri* or *A. tuberculatus* Transformed with Sterility Genes Under Specifically Regulated Promoter

*A. palmeri* or *A. tuberculatus* sterile line is being produced using 2 plasmids:

1. Plasmid encoding for a disrupter protein under a promoter that is active in the embryo or seed, which makes it sterile where the gene promoter is under the control of a specific operator sequence responsive to repression by a repressor protein.

2. A repressor protein, whose gene is under the control of a constitutive promoter. When binding to a specific chemical the repressor can bind the operator from the first plasmid and inhibit the expression of the disrupter protein. Plasmid sequences are:

1. RIP gene (ribosomal inactivating protein, sequence of a complete RIP gene, saporin 6:GenBank ID SOSAP6, Accession No. X15655) or barnase (Genbank Accession M14442) under the control of a specific embryogenesis, seed development or germination promoter with a TetO that is responsive to reverse tetracycline repressor.

2. Construction of a reverse tetracycline repressor gene under the control of a constitutive promoter.

Upon tetracycline application the reverse tetracycline repressor binds tetracycline and leads to repression of disrupter gene.

Evaluation of the efficiency of sterility in the transformed line is conducted as described in Example 10. The evaluation includes two stages:

1. Comparing the total seed number and weight between the groups.

2. Comparing the fraction of emerged seedlings out of 50 seeds sown. The experimental setup for the second stage is illustrated in the table below:

TABLE 7

| Female plants | Pollen source | Seeds count and weight | Seedling emergence estimation in progeny (as calculated from the number of seedlings emerge out of 50) |
|---|---|---|---|
| 5 female plants F | 5 males with the transformed line without tetracycline treatment $M_{T-tet}$ | $N_{seeds}(F \times M_{T-tet})$ – seed count $W_{seeds}(F \times M_{T-tet})$ – total seed weight | $N_{seedlings}(F \times M_{T-tet})$- Number of seedlings |
| 5 female plants F | 5 males with the transformed line with tetracycline treatment $M_{T+tet}$ | $N_{seeds}(F \times M_{T+tet})$ – seed count $W_{seeds}(F \times M_{T+tet})$ – total seed weight | $N_{seedlings}(F \times M_{T+tet})$- Number of seedlings |

Efficacy of Sterility by number of seeds or seedlings = $1 - (N(F \times M_{T-tet})/N(F \times M_{T+tet}))$ An alternative set of plasmids that are used are based on the Tet OFF system:

1. Plasmid encoding for a disrupter protein under a promoter that is active in the embryo or seed, which makes the plant sterile where the gene promoter is under the control of a specific operator sequence responsive to activation by an activator protein.
2. An activator protein, whose gene is under the control of a constitutive promoter. Upon specific chemical binding to this activator it becomes non-active and can no longer activate the transcription of the first plasmid.

Plasmid sequences are:

1. RIP gene (ribosomal inactivating protein, sequence of a complete RIP gene, saporin 6:GenBank ID SOSAP6, Accession No. X15655) or barnase (Genbank Accession M14442) under the control of a dual regulation with a specific embryogenesis, seed developmentor germination promoter and a TRE sequence.
2. Construction of a tetracycline transactivator protein tTA gene (composed of fusion of one protein, TetR (tetracycline repressor), found in *Escherichia coli* bacteria, with the activation domain of another protein, VP16 under the control of a constitutive promoter.

Upon application of tetracycline or its derivatives such as doxycycline the tTA becomes repressed and results in loss of activation of the disrupter gene and recovery of sterility.

Similar experimental setups are repeated with this plasmid set and the efficiency of sterility is calculated and evaluated as explained with the first plasmid set.

Example 12

Generation and Evaluation of the Susceptibility to EPSPS Inhibitor in *A. palmeri* or *A. tuberculatus* Transformed with Antisense RNA Under Specifically Regulated Promoter As in Example 10 with the use of an antisense RNA against EPSP synthase replacing the disrupter gene. EPSP synthase antisense sequence that is conserved across multiple *Amaranthus* species is used, e.g., corresponding to nucleotide positions 590-802 (antisense) of KF5692111.

Induced EPSPS inhibitor susceptibility will be examined following application of both tetracycline for activation of EPSPS antisense expression and application of EPSPS inhibitor (ROUNDUP, 360 g/l SL, MONSANTO is sprayed according to manufacturer instructions—720 g/ha) for selection.

Example 13

Generation of *A. palmeri* or *A. tuberculatus* Sterile Hybrid Line Transformed with Dual Complementary Male and Female Plant Genetic Recombinations Systems

*A. palmeri* or *A. tuberculatus* sterile line is being produced by crossing between two homozygous transformed plants.

The male and female plants are each transformed with a plasmid encoding a disrupter gene controlled by a transiently active promoter, the gene and promoter being separated by a blocking sequence flanked on either side by specific excision sequences (such as lox or frt excision sequences). In addition the plasmid contains a second gene that encodes a genetic recombination enzyme (such as cre recombinase or flp flippase) specific for the excision sequences in the opposite sex (namely, the recombination enzyme of the female plant cut the excision sequence in the male and vice versa). These recombination enzymes are under the control of a promoter that is active post seed germination stage. The transformed plasmid both in the male and in the female homozygous lines are inserted to the same genomic locus position.

The following plasmid is transformed into the female plant:

Plasmid encoding a barnase or RIP gene under the control of a specific embryogenesis or germination promoter whereas the gene and promoter being separated by a blocking sequence flanked on either side by specific excision lox sequences and a second gene encoding for a flippase recombination enzyme under a promoter that is active post seed germination.

The following plasmid is transformed into the male plant:

Plasmid encoding a barnase or RIP gene under the control of a specific embryogenesis or germination promoter whereas the gene and promoter are being separated by a blocking sequence flanked on either side by specific excision frt sequences and a second gene encoding for a cre recombinase recombination enzyme under a promoter that is active post seed germination.

Lines are being selected such that both insertions to both male and female are on the exact same genomic position.

Only upon crossing between these male plants with these female plants both recombination events by flp and cre are occurring thus yielding pollen that have a barnase or RIP gene under the control of a specific embryogenesis or germination promoter.

Example 14

Evaluation of the Sterility Property in *A. palmeri* or *A. tuberculatus* Hybrid Line Transformed with Dual Complementary Male and Female Plant Recombinase/Flippase Systems Evaluation of the efficiency of sterility in the transformed line is conducted as described in Example 10. The evaluation includes 2 stages: 1. Comparing the total seed number and weight between the two compared groups 2. Comparing the fractions of emerged seedlings out of 50 seeds sown. The experimental setup is illustrated in the table below:

TABLE 8

| Female plants | Pollen source | Seeds count and weight | Seedling emergence estimation in progeny (as calculated from the number of seedlings emerge out of 50) |
|---|---|---|---|
| 5 female plants F | 4 natural male plants M | $N_{seeds}(F \times M)$ – seed count $W_{seeds}(F \times M)$ – total seed weight | $N_{seedlings}(F \times M)$-Number of seedlings |
| 5 female plants F | 4 hybrid male plants $M_{hyb}$ | $N_{seeds}(F \times M_{hyb})$ – seed count $W_{seeds}(F \times M_{hyb})$ – total seed weight | $N_{seedlings}(F \times M_{hyb})$-Number of seedlings |

Efficacy of Sterility by number of seeds or seedlings = $1 - (N(F \times M_{hyb})/N(F \times M))$ Example 15

Achieving Reduction of *A. palmeri* or *A. tuberculatus* Population by Application of Sterile Pollen in Growth Room

*A. palmeri* or *A. tuberculatus* seeds are germinated on soil and seedlings are transferred and transplanted into pots. At flowering time two plots are being established, each of size 4×4 m, each containing together 5 female and 4 male plants.

The two plots are located in separated growth rooms in order to avoid pollen cross contamination. Sterile pollen generated as described in Example 10, 11 or 13 is dispersed on one of the plots. The application procedure is one application per day for 5 consecutive days. The plants continue to grow for 14 days and then harvested. Seed biomass is measured for each plant and the number of seeds per 0.1 g is being counted and the total number of seeds per plant is being estimated and recorded. In addition, from each female plant, 100 seeds are taken. The seeds are planted in trays of 30×30 cm. Emerged seedlings are counted at the age of 14 days and the emergence rate is calculated for both groups. The reduction in the emergence proportion between the group pollinated with sterile pollen and the control group reflects the estimation for the reduction in *A. palmeri* or *A. tuberculatus* population size due to the treatment per one reproduction cycle.

Example 16

Achieving Reduction of *A. palmeri* or *A. tuberculatus* Population by Application of Sterile Pollen in Controlled Field Conditions Sterile pollen is generated as described in Example 10, 11 or 13 and collected as described in Example 1. Two groups of 8 *A. palmeri* plants composed of 4 male plants and 4 female plants are transplanted in the field. Each group is arranged in 2 rows of four plants in alternating order of female and male. The distance between each plant is 1 m. The distance between the location of the 2 groups is 1 km. The two groups are treated similarly and are watered on a daily basis. One group is used as control group (C) to estimate the native population growth without any application of non-native pollen. The second group (T) is pollinated both with the native pollen and with additional sterile pollen that was generated as described in Examples 10, 11, or 13. At the beginning of the flowering time a pollination treatment is being applied to group T. The treatment is given in 4 applications in intervals of 3 days, each application is given once a day (at morning hours). All plants are harvested after seed maturation and seeds are being collected manually. Seed biomass is measured for each plant and the number of seeds per 0.1 g is being counted and the total number of seeds per plant is being estimated and recorded.

In addition, from each female plant, 100 seeds are taken. The seeds are planted in trays of 30×30 cm. Emerged seedlings are counted at the age of 14 days and the emergence rate is calculated for both groups. The reduction in the emergence proportion between the group pollinated with sterile pollen and the control group reflects the estimation for the reduction in *A. palmeri* or *A. tuberculatus* population size due to the treatment per one year.

TABLE 9

| Female plants | Pollen source | Seeds count and weight | Population size reduction estimation (as calculated from the number of seedlings emerge out of 100 seeds) |
|---|---|---|---|
| 5 female plants | 4 male plants | $N_{seeds}(F \times M)$ – seed count $W_{seeds}(F \times M)$ – total seed weight | $N(F \times M)$-Number of emerged seedlings |
| 5 female Plants | 4 male plants + sterile pollen | $N_{seeds}(F \times (M + M_s))$ – seed count $W_{seeds}(F \times (M + M_s))$ – total seed weight | $N(F \times (M + M_s))$-Number of emerged seedlings |

Expected population size reduction per year = $1 - N(F \times (M + M_s))/N(F \times M)$

TABLE 10

| Female plants | Pollen source | Seeds count and weight | Population size reduction estimation (as calculated from the number of seedlings emerge out of 100 seeds) |
|---|---|---|---|
| 4 female plants | 4 male plants | $N_{seeds}(F \times M)$ – seed count $W_{seeds}(F \times M)$ – total seed weight | $N(F \times M)$-Number of emerged seedlings |
| 4 female Plants | 4 male plants + sterile pollen | $N_{seeds}(F \times (M + M_s))$ – seed count $W_{seeds}(F \times (M + M_s))$ – total seed weight | $N(F \times (M + M_s))$-Number of emerged seedlings |

Expected population size reduction per year = $1 - N(F \times (M + M_s))/$

Example 17

Achieving Reduction of *A. palmeri* or *A. tuberculatus* Population by Application of Sterile Pollen from a Natural Seedless Strain in Growth Room Pollen is collected from naturally occurring seedless strain of *A. palmeri* or *A. tuberculatus*. This pollen is used as described in Example 15 to evaluate the efficacy of the sterility achieved.

Example 18

Achieving Sterility in *A. palmeri* or *A. tuberculatus* by Applying Pollen Harvested from Tetraploid *A. palmer* Strain Generation of *A. palmeri* or *A. tuberculatus* tetraploid plants is achieved by treatment of 0.25% aqueous solution of colchicine on growing buds of seedling thrice daily for three consecutive days. Pollen from these plants is harvested and collected.

This pollen is used as described in Example 15 to evaluate the efficacy of the sterility achieved.

Example 19

Achieving Sterility in *A. palmeri* or *A. tuberculatus* by Applying Pollen Pre-Treated with Irradiation Pollen from naturally occurring *A. palmeri* or *A. tuberculatus* plants is harvested and collected. The pollen is treated by UV, X-ray or gamma irradiation. This pollen is used as described in Example 15 to evaluate the efficacy of the sterility achieved.

Example 20

Achieving Reduction of *A. palmeri* and *A. tuberculatus* Populations by Application of Mixture of Sterile Pollen in a Controlled Field Conditions Sterile pollen is generated as described in Examples 10, 11, 13, 17, 18 or 19 and collected as described in Example 1 both from *A. palmeri* male plants and from *A. tuberculatus* male plants. The pollen from both species is mixed together and the treatment is with this mixture. The field experimental setup is similar to the one described in Example 16 except that instead of having in each group 8 *A. palmeri* plants (composed of 4 female and 4 males plants) each group contains 4 *A. palmeri* plants (2 females and 2 males) and 4 *A. tuberculatus* plants (2 females and 2 males). At the beginning of flowering time one group is being treated with the pollen mixture 1 application per day for 4 times in intervals of 3 days.

The effect of pollen treatment on the population size of both species is estimated similarly to the way described in example 16.

TABLE 11

| Female plants | Pollen source | Population size reduction estimation (as calculated from the number of seedlings emerge out of 100 seeds) |
|---|---|---|
| 2 *A. palmeri* + 2 *A. tuberculatus* | 2 *A. palmeri* + 2 *A. tuberculatus* | $N_p(F \times M)$-Number of *A palmeri* emerged seedlings $N_t(F \times M)$-Number of *A. tuberculatus* emerged seedlings |
| 2 *A. palmeri* + 2 *A. tuberculatus* | 2 *A. palmeri* + 2 *A. tuberculatus* + mixture of sterile pollen | $N_p(F \times (M + M_s))$-Number of *A. palmeri* emerged seedlings $N_t(F \times (M + M_s))$-Number of *A. tuberculatus* emerged seedlings |

Expected population size reduction per year = $1 - N_{p/t}(F \times (M + M_s))/N_{p/t}(F \times M)$

Example 21

Generation and Evaluation of Induced EPSPS Inhibitor Susceptibility Following *A. palmeri* or *A. tuberculatus* Transformation with AlcR Based Ethanol Inducible Death Gene

*A. palmeri* or *A. tuberculatus* EtoH inducible line is being produced using a plasmid encoding for AlcR based EtoH inducible promoter linked to a barnase gene or a RIP gene. In this example there is no repression or tissue specific promoter. The promoter is activated after EtoH spraying and therefore, the seeds do not develop.

*A. palmeri* transformation is carried out as previously described in Pal A., et al 2013 to *A. tricolor*, supra. A stable transformed line that highly expresses the desired plasmids is selected for further stages.

Pollen collected from this line are examined in a similar protocol as explained in Example 4 except that seeds are sprayed with EtoH instead of the herbicide used in that example to evaluate the efficiency of death following EtoH application.

Example 22

Generation and Evaluation of Induced Death Following *A. palmeri* or *A. tuberculatus* Transformation with AlcR Based Ethanol Inducible EPSPS Antisense RNA As in Example 21 with the use of an antisense RNA against EPSP synthase replacing the disrupter gene. EPSP synthase antisense sequence that is conserved across multiple *Amaranthus* species is used, e.g., corresponding to nucleotide positions 597-809 (antisense) of FJ861243.1.

Induced EPSPS inhibitor susceptibility will be examined following application of both EtOH for activation of EPSPS antisense expression and application of EPSPS inhibitor (ROUNDUP, 360 g/l SL, MONSANTO is sprayed according to manufacturer instructions—720 g/ha) for selection.

Example 23

Demonstration of Seed Production Via Artificial Pollination in *A. palmeri*

*A. palmeri* seeds were germinated on paper and the seedlings were transferred into small pots. After the plants reached a height of about 20 cm they were transferred again into larger pots. When plants began flowering, they were closely monitored daily to identify their sex at an early stage. Immediately after sex identification the females and males were separated and placed in different locations (~6 m apart) outside on September-October in Israel.

Pollen was collected at early morning from *A. palmeri* male plants using paper tubes (12 cm in length and a diameter of ~1 cm). Each such paper tube was placed on a single male spike. Pollen was released by gently tapping on the paper tube. Each paper tube was used to pollinate an *A. palmeri* female spike by placing it (with the pollen inside) on one spike and gently tapping it (tapping procedure was repeated several times at intervals of ~10 minutes to enhance pollination). The procedure of artificial pollination was repeated for several days (2-3 times) for each spike and the entire experiment was repeated 3 times—overall 8 spikes (first experiment—2 spikes, second experiment—2 spikes, third experiment—4 spikes were pollinated and 7 spikes served as controls with no application of pollen (first experiment—2 spikes, second experiment—2 spikes, third experiment—3 spikes). The total number of seeds formed (15-20 days post initial pollination event) from each spike and their weights were measured and the results are depicted in Table 12 below:

TABLE 12

| # Exp | # of control spikes | # of pollinated spikes | Control seeds Avg. sample weight (g) | Pollinated seeds Avg. sample weight (g) | Fold Change Pollinated/ Control | P-value |
|---|---|---|---|---|---|---|
| 1 | 2 | 2 | 0.07 | 0.18 | 2.52 | 0.06 |
| 2 | 2 | 2 | 0.05 | 0.14 | 2.77 | 0.15 |
| 3 | 3 | 4 | 0.041 | 0.145 | 3.67 | 0.0078 |
| Combined data | 7 | 8 | 0.052 | 0.155 | 2.96 | 2.36E−5 |

As can be seen from the table artificial pollination significantly increase the amount of seeds formed.

To evaluate the quality of the seeds that were obtained, average seed weight was calculated and compared to average seed weight of seeds that were collected directly from the field. Results demonstrated that natural seeds and seeds obtained from artificial pollination had a similar weight (see FIG. 1).

Example 24

Inhibition of Seed Development and Demonstration of Weed Control by Reduced Seed Germination in *A. palmeri* by Applying X-Ray Irradiated Pollen in Growth Room

*A. palmeri* seeds were germinated on paper and the seedlings were transferred into small pots. After the plants reached a height of about 20 cm they were transferred into larger pots. When plants began flowering, they were closely monitored daily to identify their sex at an early stage. Immediately after sex identification the females and males were separated and placed in different growth rooms in order to avoid pollination. One female plant with relatively many flowering spikes was transferred into a growth chamber (conditions of 30°/22° C., photoperiod 16/8 day/night) where the pollination experiment was conducted.

Pollen was collected at early morning from *A. palmeri* male plants using paper tubes (12 cm in length and a diameter of ~1 cm). Each such paper tube was placed on a single male spike. Pollen was released by gently tapping on the paper tube. Eight such paper tubes with fresh pollen were collected and divided into two sets of 4. Each set of 4 paper tubes was placed in a 15 cm petri dish. One petri dish was irradiated by X-ray radiation of 300 Gy (overall the duration of the radiation was 80 minutes) while the other petri dish was placed for that time in similar conditions only without radiation and served as a control with non-irradiated pollen. About 2 hours after pollen collection it was used to artificially pollinate 8 spikes of a female *A. palmeri* plant. These 8 spikes were divided into 4 pairs where the height of the branch origin of each such pair was approximately the same. Each paper tube was used to pollinate an *A. palmeri* female spike by placing it (with the pollen inside) on one spike and gently tapping it (tapping procedure was repeated several times in intervals of ~15 minutes to enhance pollination). Pollination was conducted such that one spike from each pair was pollinated with the irradiated pollen and the other with non-irradiated pollen (overall 4 pairs were pollinated). Additional 2 empty paper tubes with no pollen inside were placed on additional 2 spikes in order to serve as a "no-pollen" control. The paper tubes were removed from the spikes after about an hour. 18 days after pollination the top 12 cm of each of the 10 spikes was cut and seeds were harvested. Total seed weight and total seed count per spike were measured and seed morphology was examined.

The results are depicted in Table 13, below.

TABLE 13

| Sample | Total Seed Weight (gr) | Number of Seeds | Average Seed Weight (mgr) |
|---|---|---|---|
| Regular pollen #1 | 0.0769 | 214 | 0.359 |
| Regular pollen #2 | 0.0777 | 221 | 0.352 |
| Regular pollen #3 | 0.0936 | 317 | 0.295 |
| Regular pollen #4 | 0.0589 | 227 | 0.259 |
| Irradiated pollen #1 | 0.0173 | 181 | 0.096 |
| Irradiated pollen #2 | 0.0193 | 183 | 0.105 |
| Inadiated pollen #3 | 0.0152 | 134 | 0.113 |
| Irradiated pollen #4 | 0.0067 | 105 | 0.064 |
| No-pollen | 0.0011 | 1 | NA |
| No-pollen | 0 | 0 | NA |
| Average value for regular pollen | 0.076775 | 244.75 | 0.316417252 |
| Average value for irradiated pollen | 0.014625 | 150.75 | 0.094571738 |
| t-test p-value | 0.00018 | 0.022 | 0.00015 |

Figure 1:
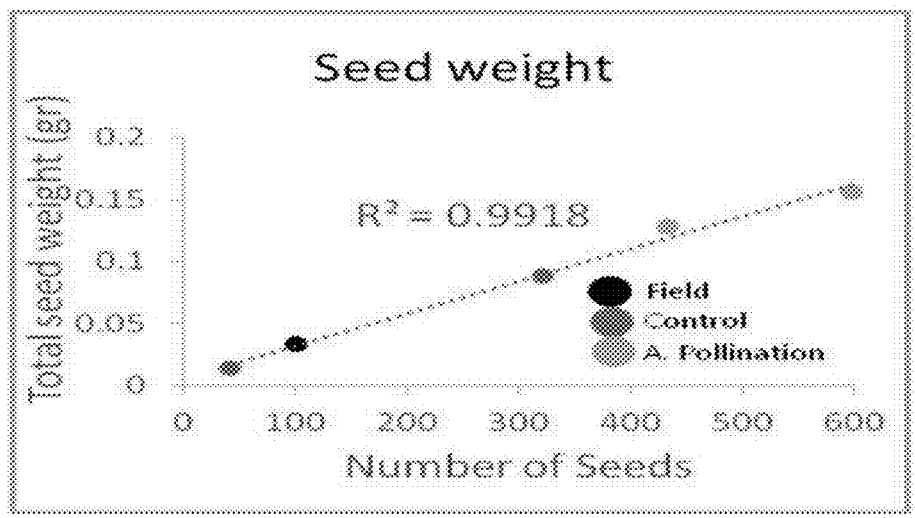
Figure 2:
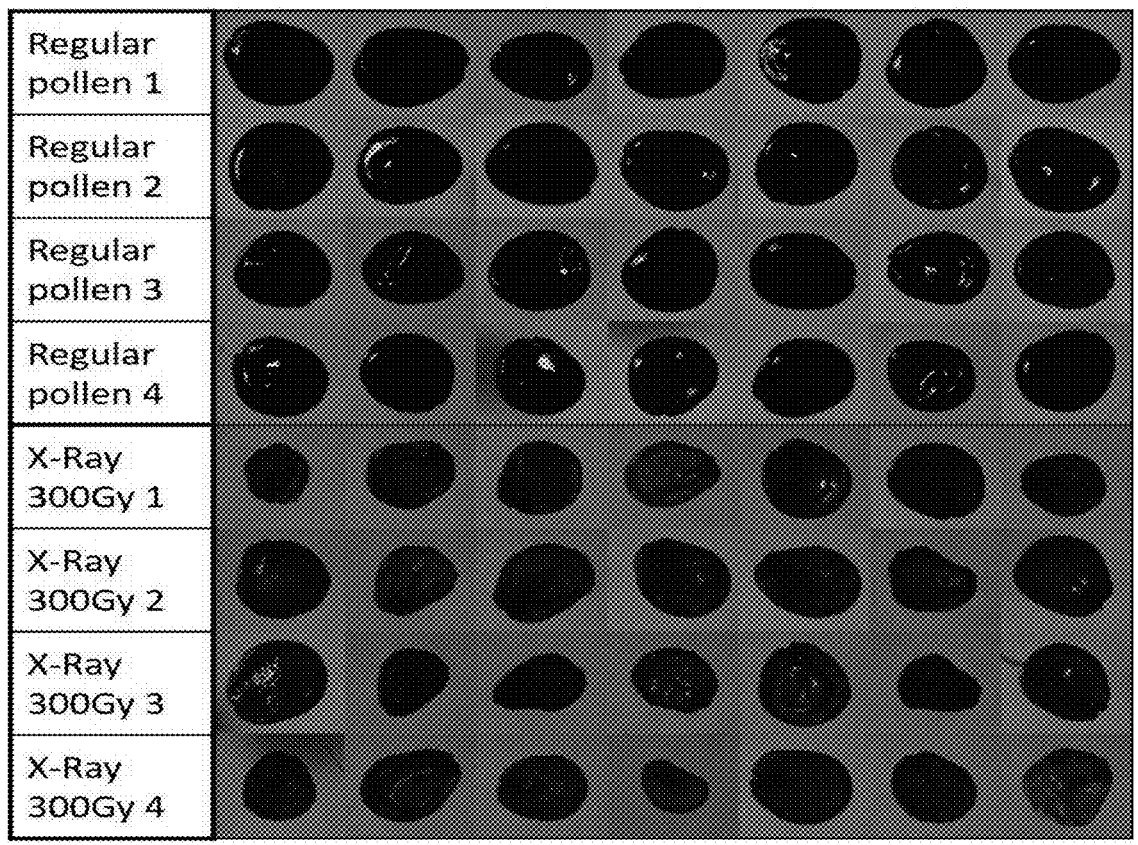

Seeds were examined under the microscope and for each sample pictures were taken for a random assortment of seeds with representative appearance (See FIG. 2). In general, the seeds obtained from the artificial pollination with the irradiated pollen looked thin, partly empty and their color was light brown while the ones obtained from the regular pollen looked more filled having a darker brown/black color.

Germination assay was conducted in order to estimate the different germination levels between the seeds obtained by artificial pollination with the irradiated pollen versus the ones obtained from artificial pollination with regular pollen.

Thirty seeds were taken from each of these 8 samples. Each set of 30 seeds was placed in a 6 cm petri dish on a towel paper with 7.5 ml tap water for the germination test. These petri dishes were sealed with parafilm and were placed in a growth chamber in 34/25° C. 16/8 h day/night conditions for 16 days. After 16 days emerged seedlings were counted and germination rate was calculated for each sample. A comparison was conducted between the seeds obtained from irradiated pollen and the ones obtained from regular pollen. While the average germination rate obtained from the regular pollen was approximately 72% none of the seeds obtained from artificial pollination with irradiated pollen germinated (p value of 2.43E-05).

The results are summarized in Table 14, below.

TABLE 14

| Sample | Germination Rate (%) |
|---|---|
| Regular pollen #1 | 73.33333 |
| Regular pollen #2 | 70 |
| Regular pollen #3 | 86.66667 |
| Regular pollen #4 | 56.66667 |
| Irradiated pollen #1 | 0 |
| Irradiated pollen #2 | 0 |
| Irradiated pollen #3 | 0 |
| Irradiated pollen #4 | 0 |
| Average value for regular pollen | 71.66667 |
| Average value for irradiated pollen | 0 |
| t-test p-value | 2.43E-05 |

The same experiment was conducted with an additional female plant in a similar manner only with 2 samples of X-ray irradiated pollen vs. 2 samples of non-irradiated pollen controls and a single "no-pollen" control. The results are depicted in Table 15 below.

TABLE 15

| Sample | Total Seed Weight (gr) | Number of Seeds | Average Seed Weight (mgr) |
|---|---|---|---|
| Regular pollen #1 | 0.0486 | 247 | 0.197 |
| Regular pollen #2 | 0.0401 | 202 | 0.199 |
| Inadiated pollen #1 | 0.0192 | 173 | 0.110 |
| Irradiated pollen #2 | 0.0138 | 170 | 0.081 |
| No-pollen | 0.0065 | 5 | NA |
| Average value for regular pollen | 0.04435 | 224.5 | 0.198 |
| Average value for irradiated pollen | 0.0165 | 171.5 | 0.096 |
| t-test p-value | 0.031 | 0.143 | 0.020932284 |

Figure 3:
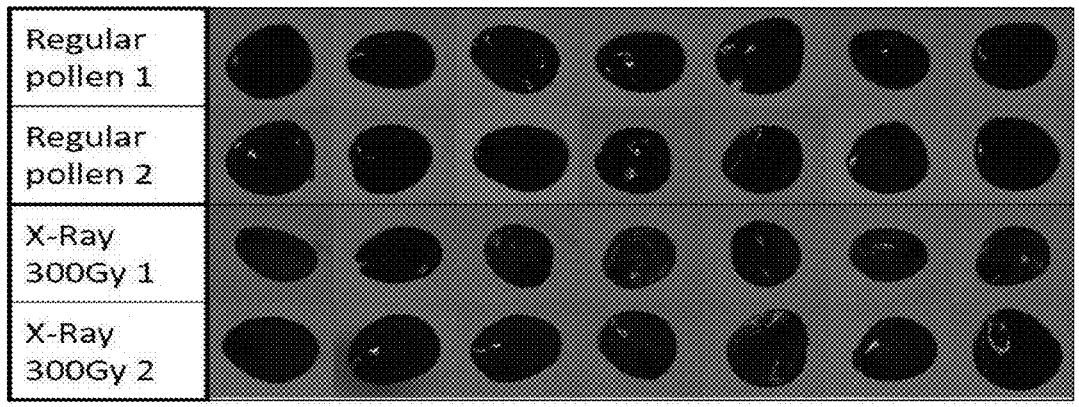

Seeds were examined under the microscope and for each sample pictures were taken for a random assortment of seeds with representative appearance (See FIG. 3). In general, the seeds obtained from the artificial pollination with the irradiated pollen looked thinner, partly empty and their color was lighter brown relative to the ones obtained from the regular pollen, which looked more filled, having a darker brown/black color.

A germination test was conducted as described above. The germination rates obtained are provided in Table 16 below.

TABLE 16

| Sample | Germination Rate (%) |
|---|---|
| Regular pollen #1 | 56.66667 |
| Regular pollen #2 | 16.66667 |
| Irradiated pollen #1 | 0 |
| Irradiated pollen #2 | 0 |
| Average value for regular pollen | 36.66667 |
| Average value for irradiated pollen | 0 |
| t-test p-value | 0.21 |

Overall, the results indicate that upon application of X-ray irradiated pollen, the seeds that are formed display seed development arrest with reduced number, weight and altered morphology and furthermore these seeds are devoid of their ability to germinate.

Example 25

Evaluation of *A. palmeri* Weed Control Efficiency by Artificial Pollination with UV Irradiated Pollen in Growth Room

*A. palmeri* seeds were germinated on paper and the seedlings were transferred into small pots. After the plants reached a height of about 20 cm they were transferred into larger pots. When plants began flowering, they were closely monitored daily to identify their sex at an early stage. Immediately after sex identification the females and males were separated and placed in different growth rooms in order to avoid pollination. One female plant with relatively many flowering spikes was transferred into a growth chamber (conditions of 34°/25° C., photoperiod 16/8 day/night) where the pollination experiment was conducted.

Pollen was collected at early morning from *A. palmeri* male plants using paper tubes (10 cm in length and diameter of ~1 cm). Each such paper tube was placed on a single male spike. Pollen was released by gently tapping on the paper tube. Six such paper tubes with fresh pollen were collected and divided into two sets of 3. Each set of 3 paper tubes was placed in a 15 cm petri dish. Each such paper tube was cut and opened carefully and was organized and placed with pollen exposed from the upper direction. One petri dish was put into UVITEC cross-linker machine for irradiation by UV-C (wave length of 254 nm) with energy of 2 joules. Total radiation time was 10 minutes. During this time the other petri dish was placed in similar conditions only without the irradiation treatment. After the irradiation procedure ended the opened paper tubes were re-attached to a cylindrical shape and each one of them was used to pollinate an *A. palmeri* female spike (in total 6 spikes) by placing it (with the pollen inside) on one spike and gently tapping it (tapping procedure was repeated several times in intervals of ~15 minutes to enhance pollination). These 6 female spikes were originally divided into 3 pairs where the height of the branch origin of each such pair was approximately the same and pollination was conducted such that one spike from each pair was pollinated with the irradiated pollen and the other with non-irradiated pollen (overall 3 pairs were pollinated). The paper tubes were removed from the spikes after about an hour. 17 days after pollination, the top 10 cm of each of the 6 pollinated spikes plus additional 2 non-artificially pollinated spikes (that served as a "no-pollen" control) were cut and seeds were harvested. Total seed weight and total seed count per spike were measured and the results are depicted in Table 17 below.

TABLE 17

| Sample | Total Seed Weight (gr) | Number of Seeds | Average Seed Weight (gr) |
|---|---|---|---|
| Regular pollen #1 | 0.0506 | 157 | 0.000322 |
| Regular pollen #2 | 0.0927 | 263 | 0.000352 |
| Regular pollen #3 | 0.0447 | 108 | 0.000414 |
| Irradiated pollen #1 | 0.0078 | 12 | 0.00065 |
| Irradiated pollen #2 | 0.0315 | 48 | 0.000656 |
| Irradiated pollen #3 | 0.0053 | 7 | 0.000757 |

TABLE 17-continued

| Sample | Total Seed Weight (gr) | Number of Seeds | Average Seed Weight (gr) |
|---|---|---|---|
| No-pollen | 0 | 0 | |
| No-pollen | 0 | 0 | |
| Average value for regular pollen | 0.062666667 | 176 | |
| Average value for irradiated pollen | 0.014866667 | 22.33333 | |
| t-test p-value | 0.050404957 | 0.031884 | |

Overall, the results indicate that upon application of UV irradiated pollen a reduction in the number of seeds obtained is demonstrated compared to application of regular pollen.

Example 26

Evaluation of *A. palmeri* Weed Control Efficiency by Artificial Pollination with Gamma Irradiated Pollen in Growth Room The experiment was conducted similar to Example 24 (X-ray) with the difference that the pollen is irradiated by gamma irradiation with the following radiation intensities: 100, 300 and 500 Gy and compared to regular (non-irradiated) pollen as a control. The size of the paper tubes that were used for pollen collection and for artificial pollination was 6 cm in length. 4 paper tubes were used for each condition: non-irradiated pollen, 100 Gy, 300 Gy and 500 Gy. Additionally, 3 empty paper tubes were used in order to estimate the background level of seed production without pollination. 16 days after the artificial pollination stage, the pollinated spikes were cut and seeds were harvested. In order to evaluate the efficiency of the treatments, total seed weight, seed number and average weight per seed in each sample were measured and the average values for each treatment were compared.

The results are depicted in Table 18, below.

TABLE 18

| Sample | Total Seed Weight (gr) | Number of Seeds | Average Seed Weight (mgr) |
|---|---|---|---|
| Regular pollen #1 | 8.27E−02 | 231 | 3.58E−01 |
| Regular pollen #2 | 6.03E−02 | 212 | 2.84E−01 |
| Regular pollen #3 | 7.98E−02 | 234 | 3.41E−01 |
| Regular pollen #4 | 6.82E−02 | 219 | 3.11E−01 |
| Irradiated pollen (100 Gy) #1 | 6.64E−02 | 231 | 2.87E−01 |
| Irradiated pollen (100 Gy) #2 | 7.51E−02 | 270 | 2.78E−01 |
| Irradiated pollen (100 Gy) #3 | 8.84E−02 | 291 | 3.04E−01 |
| Irradiated pollen (100 Gy) #4 | 3.29E−02 | 107 | 3.07E−01 |
| Irradiated pollen (300 Gy) #1 | 2.91E−02 | 157 | 1.85E−01 |
| Irradiated pollen (300 Gy) #2 | 3.72E−02 | 241 | 1.54E−01 |
| Irradiated pollen (300 Gy) #3 | 2.74E−02 | 183 | 1.50E−01 |
| Irradiated pollen (300 Gy) #4 | 3.18E−02 | 246 | 1.29E−01 |
| Irradiated pollen (500 Gy) #1 | 1.35E−02 | 96 | 1.41E−01 |
| Irradiated pollen (500 Gy) #2 | 6.90E−03 | 80 | 8.63E−02 |
| Irradiated pollen (500 Gy) #3 | 7.90E−03 | 106 | 7.45E−02 |
| Irradiated pollen (500 Gy) #4 | 4.90E−03 | 120 | 4.08E−02 |
| No-pollen #1 | — | 2 | — |
| No-pollen #2 | — | 6 | — |
| No-pollen #3 | — | 14 | — |
| Average value for regular pollen | 7.27E−02 | 224 | 0.32 |
| Average value for irradiated pollen (100 Gy) | 6.57E−02 | 224.75 | 0.29 |
| Average value for irradiated pollen (300 Gy) | 3.13E−02 | 206.75 | 0.15 |
| Average value for irradiated pollen (500 Gy) | 8.30E−03 | 100.5 | 0.09 |
| t-test p-value (100 Gy versus regular pollen) | 6.05E−01 | 9.86E−01 | 1.45E−01 |
| t-test p-value (300 Gy versus regular pollen) | 3.17E−04* | 4.72E−01 | 1.45E−04* |
| t-test p-value (500 Gy versus regular pollen) | 2.34E−05* | 1.59E−05* | 1.02E−04* |

*P-value < 0.001

The data in the table demonstrates a significant decrease in total seed weight and weight per seed following pollination with the gamma irradiated pollen (300 Gy and 500 Gy) relatively to the ones obtained by regular pollen. In addition, seed number was also decreased significantly following the 500 Gy irradiation treatment.

Figure 4:
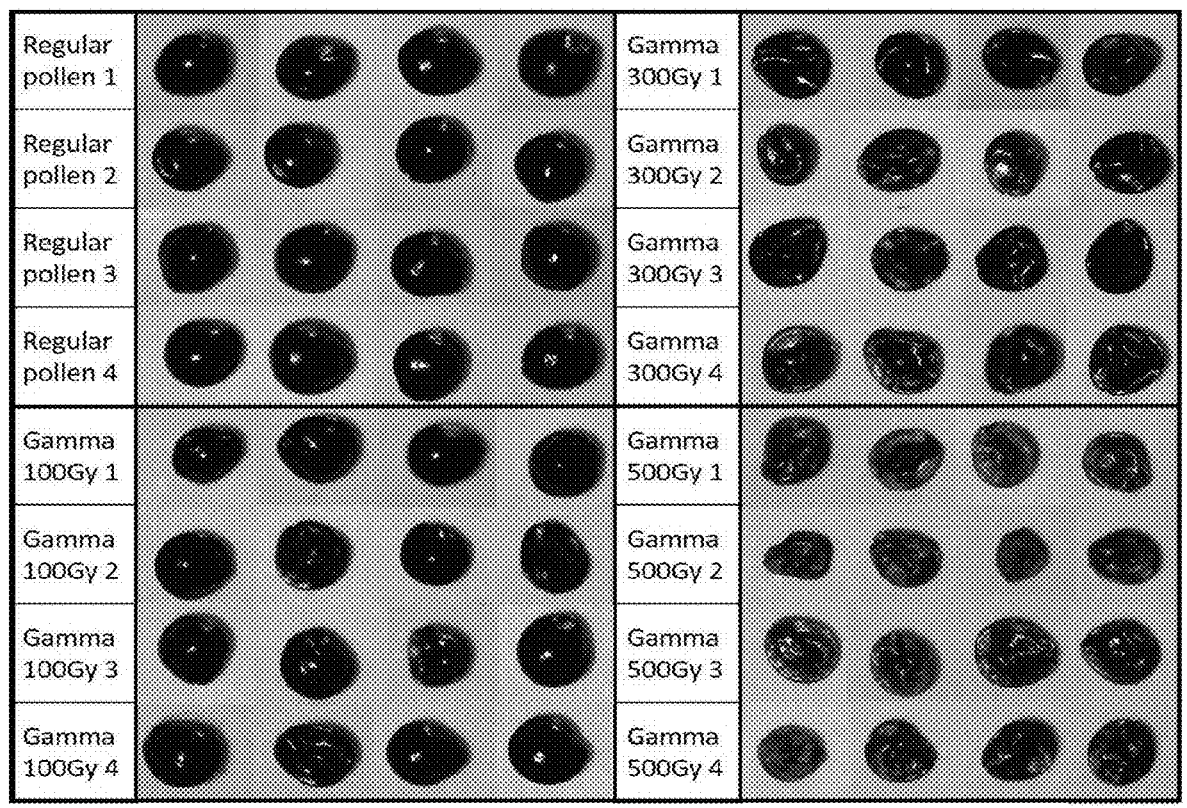

In addition, seed morphology was examined and compared to evaluate seed development. To that end seeds were examined under the microscope and for each sample pictures were taken for a random assortment of seeds with representative appearance (See FIG. 4). In general, the seeds obtained from the artificial pollination with the irradiated pollen looked thinner, partly empty and their color was lighter relative to the ones obtained from the regular pollen, which looked more filled, having a black color.

An additional repeat was conducted on a separate plant with conditions of regular (non-irradiated) pollen, 100 Gy and 300 Gy with one sample for each. It yielded a very similar trend. As shown in Table 19 below and in FIG. 5:

TABLE 19

| Sample | Total Seed Weight (gr) | Number of Seeds | Average Seed Weight (mgr) |
|---|---|---|---|
| Regular pollen | 1.23E−01 | 229 | 5.39E−01 |
| Irradiated pollen (100 Gy) | 1.74E−01 | 337 | 5.16E−01 |
| Irradiated pollen (300 Gy) | 5.56E−02 | 259 | 2.14E−01 |
| No-pollen #1 | — | 0 | — |

Overall, the results indicate that upon application of gamma irradiated pollen, the seeds that are formed display seed development arrest with reduced number, weight and altered morphology.

Example 27

Evaluation of *A. palmeri* Weed Control Efficiency by Artificial Pollination with Chromosomally Aberrant Pollen in Growth Room

*A. palmeri* Seeds are germinated for 8 hours at a temperature of 34° C. in distilled water. Thereafter seeds are soaked in solutions with 3 different colchicine concentrations: 0.1%, 0.5% 1% with or without the addition of 1% DMSO. (Chen et al., 2004, Castro et al., 2003, Soo Jeong Kwon et al., 2014, Roselaine Cristina Pereiral et al.). The soaking procedure is conducted for 4 or 20 hours at 34° C. Finally, the seeds are washed and seeded in a 6 cm petri dish on a towel paper with 7.5 ml tap water. The petri dishes are sealed with parafilm and are placed in a growth chamber at 34/25° C. 16/8 h day/night conditions. One week later, seedlings are transferred into germination beds. Samples are taken to evaluate their chromosome set. The plants are then grown until reaching the flowering stage. Male plants with various chromosomal abnormalities (e.g., polyploidy, tetraploidy) are selected for an additional examination. Pollen is collected from these plants and tested for its ability to germinate in-vitro and to fertilize. Selected pollen is applied onto *A. palmeri* diploid female plants. Total seed weight, seed number, seed morphology and seed germination are examined in comparison to seeds obtained from pollination with regular diploid pollen as explained in Examples 24-26.

Example 28

Achieving Reduction of *A. palmeri* or *A. tuberculatus* Population by Application of Sterile Pollen in Controlled Field Conditions Sterile pollen is generated as described in Example 17, 18, 19 24, 25, 26 or 27 and collected as described in Example 1. Experiment is conducted similarly to Example 16 to evaluate weed control efficiency.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Other References are Cited in the Application

1. Schnable and Wise. (1998). The molecular basis of cytoplasmic male sterility and fertility restoration. Trends in Plant Science. 3, 175-180.
2. Oerke, E-C. (2006) Crop losses to pests. J Agric. Sci. 144, 31-43
3. Pimentel, D. et al. (2000) Environmental and economic costs of nonindigenous species in the United States. BioScience 50, 53-65
4. Delye et al. (2013) Deciphering the evolution of herbicide resistance in weeds. Trends in Genetics 29, 649-658
5. Klassen, W., C. F. Curtis (2005). History of the sterile insect technique, pp. 3-36 In V. A. Dyck, J. Hendrichs, and A. S. Robinson. The Sterile Insect Technique: Principles and Practice in Area-Wide Integrated Pest Management. Springer, Dordrecht, The Netherlands. 787 PP.
6. Yosiaki I T O et al. (2003) Eradication of the Melon Fly, Bactroceracucurbitae, from Okinawa, Japan, by Means of the Sterile Insect Technique, with Special Emphasis on the Role of Basic Studies, Journal of Asia-Pacific Entomology. 6, 119-129.
7. Kohama, T et al. (2003) A progress report on the eradication program of the sweet potato weevil, *Cylasformicarius* (Fabricius) (Coleoptera: Brentidae), with both male annihilation using sex pheromone and sterile insect releases in Kume Island, Okinawa, Japan, pp. 65-69. In Recent trends on sterile insect technique and area-wide integrated pest management—economic feasibility, control projects, farmer organization and *Bactrocera dorsalis* complex control study. Research Institute for Subtropics, Okinawa, Japan.
8. Pandey et al. (2006) Zinc is critically required for pollen function and fertilisation in lentil. Journal of Trace Elements in Medicine and BiologyVolume 20, Issue 2, Pages 89-96
9. Bhalla et al. (2001) Reduction in allergenicity of grass pollen by genetic engineering. Int Arch Allergy Immunol. 124(1-3):51-4.

10. Sauer, J. D. (1972) The dioecious amaranths: a new species name and major range extensions. Madrono 21:426-434.
11. Ribeiro, D. N. et al. (2012) Apomixis involvement in inheritance of glyphosate resistance in *Amaranthus palmeri* from Mississippi. Abstracts of the Weed Science Society of America Annual Meeting. www(dot)wssaabstracts(dot)com/public/9/abstract-438(dot)html.
12. Schernthaner, J. P. et al. (2003) Control of seed germination in transgenic plants based on the segregation of a two-component genetic system. PNAS 100(11):6855-6859.
13. Gaines, T. A et al. (2012) Interspecific hybridization transfers a previously unknown glyphosate resistance mechanism in *Amaranthus* species. Evolutionary Applications 5(1):29-38.
14. Padidam et al. (2003) Chemically regulated gene expression in plants. Curr Opin Plant Biol. 6(2):169-77.
15. Hughes, D. W., and Galau, G. A. (1989) Temporally modular gene expression during cotyledon development, Genes and Development 3:358-369.
16. Horak M J et al. (1997) Control and cross-resistance of an acetolactate synthase inhibitorresistant palmer amaranth (*Amaranthus palmeri*) biotype Weed Technology 11(1):p 132
17. Patzoldt W L et al (2002). Variable herbicide response among Illinois waterhemp (*Amaranthus rudis* and *A. tuberculatus*) populations. Crop Prot 21: 707-712
18. Culpepper A S et al. (2006). Glyphosate-resistant Palmer amaranth (*Amaranthus palmeri*) confirmed in Georgia. Weed Science 54(4):620-626.
19. Agriculture Research Service National Plant Germplasm System plant introduction
20. Vijay K. et al. (2013) Glyphosate Resistance in Tall Waterhemp (*Amaranthus tuberculatus*) from Mississippi is due to both Altered Target-Site and Nontarget-Site Mechanisms. Weed Science 61(3):374-383.
21. Heap, I. The International Survey of Herbicide Resistant Weeds.
22. Matzrafi M and Baruch R (2015) Multiple herbicide resistance in rigid ryegrass (*Lolium rigidum*) in Israel. The 6$^{th}$ international weed science congress.
23. Khraiwesh, B. et al. (2012) Role of miRNAs and siRNAs in biotic and abiotic stress responses of plants. Biochim Biophys Acta. 1819(2): 137-148
24. Santos-Mendoza et al., (2008) Deciphering gene regulatory networks that control seed development and maturation in *Arabidopsis*.
25. Pedrosa A M, et al., (2015) Late Embryogenesis Abundant (LEA) Constitutes a Large and Diverse Family of Proteins Involved in Development and Abiotic Stress Responses in Sweet Orange (*Citrus sinensis* L. Osb). 10(12).e0145785
26. Le B H et al., (2010) Global analysis of gene activity during *Arabidopsis* seed development and identification of seed-specific transcription factors. PNAS 26 107(18) 8063-8070.
27. McElver J et al., (2001) Insertional Mutagenesis of Genes Required for Seed Development in *Arabidopsis thaliana*. Genetics 159: 1751-1763.
28. Chen F, Bradford K J (2000) Expression of an expansion is associated with endosperm weakening during tomato seed germination. Plant Physiol. 124:1265-1274.
29. Nonogaki H, Gee O H, Bradford K J: A germination-specific endo β mannanase gene is expressed in the micropylar endosperm cap of tomato seeds. Plant Physiol 2000, 123:1235-1246.
30. Leubner-Metzger G, Meins F: Sense transformation reveals a novel role for class I β-1,3-glucanase in tobacco seed germination. Plant J 2000, 23:215-221. A functional analysis of the role of 1,3 glucanases in seed germination.
31. Wu C T, Leubner-Metzger G, Meins F, Bradford K J: Class I β-1,3-glucanase and chitinase are expressed in the micropylar endosperm of tomato seeds prior to radicle emergence. Plant Physiol 2001, 126:1299-1313.
32. Toorop P E, van Aelst A C, Hilhorst H W M: The second step of the biphasic endosperm cap weakening that mediates tomato (*Lycopersicon esculentum*) seed germination is under control of ABA. J Exp Bot 2000, 51:1371-1379.
33. Dubreucq B, Berger N, Vincent E, Boisson M, Pettetier G, Caboche M, Lepiniec L: The *Arabidopsis* AtERP1 extensin-like gene is specifically expressed in endosperm during seed germination. Plant J 2000, 23:643-652.
34. Shu K et al. (2015) Dormancy and germination: How does the crop seed decide?Plant Biol. 1104-1112:(6)17
35. Jofre-Garfias, A E et al., (1997) *Agrobacterium*-mediated transformation of *Amaranthus hypochondriacus*: light- and tissue-specific expression of a pea chlorophyll a/b-binding protein promoter. Plant Cell Rep. 16, 847-852.
36. Swain et al., (2010)*Agrobacterium*×plant factors influencing transformation of 'Joseph's coat' (*Amaranthus tricolor* L.) Scientia Horticulturae 125:461-468.
37. Pal A. et al. (2013) *Agrobacterium* pRi TL-DNA rolB and TR-DNA Opine Genes Transferred to the Spiny Amaranth (*Amaranthus spinosus* L.), A Nutraceutical Crop, Food Technol. Biotechnol. 51 26-35.
38. Atkinson, N J and Urwin, P E (2012) The interaction of plant biotic and abiotic stresses: from genes to the field. J Exp Bot. 63(10):3523-3543.
39. Chen et al., (2004) The development of an *Arabidopsis* model system for genomewide analysis of polyploidy effects. Biol J Linn Soc Lond.; 82(4): 689-700.
40. Castro et al., (2003) Changes in allele frequencies in colchicines-treated ryegrass populations assessed with RAPD markers. Agrociencia 9: 107-112.
41. Soo Jeong Kwon et al., (2014) Tetraploid induction approach induced by colchicine of *Prunella vulgaris* for. albiflora Nakai. International Journal of Scientific and Research Publications, Volume 4, Issue 12, ISSN 2250-3153
42. Roselaine Cristina Pereira et al., (2014) Chromosome duplication in *Lolium multiflorum* Lam. Crop Breeding and Applied Biotechnology 14: 251-255

Terminator patent—U.S. Pat. No. 5,723,765
Reverse sterility patents—AU621195, U.S. Pat. No. 5,808,034

What is claimed is:

1. A method of producing pollen that reduces fitness of at least one weed species of interest, the method comprising treating the pollen of plants of at least one weed species selected from the group consisting of *Amaranthus palmeri* and *Amaranthus tuberculatus* with an irradiation regimen of X-ray radiation at an irradiation dose of 100-300 Gy, with the proviso that when said weed species is *A. palmeri* and said irradiation is X-ray, the irradiation dose is not 300 Gy.

2. The method of claim 1, wherein said pollen is a non-harvested pollen.

3. The method of claim 2, further comprises harvesting the pollen following said treating.

4. The method of claim 1, wherein said plants of said weed species of interest comprise only male plants.

5. The method of claim 1, wherein said plants are grown in a large scale setting.

6. The method of claim 5, wherein said large-scale setting essentially does not comprise crops.

7. The method of claim 1, wherein said pollen that reduces fitness manifests its effect in the first generation after fertilization.

* * * * *